US008637707B2

(12) United States Patent
Keil et al.

(10) Patent No.: US 8,637,707 B2
(45) Date of Patent: Jan. 28, 2014

(54) METHOD FOR PRODUCING AMINOBIPHENYLENE

(75) Inventors: Michael Keil, Freinsheim (DE); Michael Rack, Eppelheim (DE); Thomas Zierke, Boehl-Iggelheim (DE); Markus Heinrich, Friedberg (DE); Alexander Wetzel, Gundelfingen (DE)

(73) Assignees: BASF SE, Ludwighsafen (DE); Technische Universitaet Muenchen, Munich (DE)

( * ) Notice: Subject to any disclaimer, the term of this patent is extended or adjusted under 35 U.S.C. 154(b) by 283 days.

(21) Appl. No.: 13/001,685

(22) PCT Filed: Jul. 3, 2009

(86) PCT No.: PCT/EP2009/058457
§ 371 (c)(1),
(2), (4) Date: Dec. 28, 2010

(87) PCT Pub. No.: WO2010/000856
PCT Pub. Date: Jan. 7, 2010

(65) Prior Publication Data
US 2011/0105760 A1 May 5, 2011

(30) Foreign Application Priority Data

Jul. 3, 2008 (EP) .................................. 08159632
Oct. 15, 2008 (EP) .................................. 08166713

(51) Int. Cl.
*C07D 209/60* (2006.01)
*C07C 209/68* (2006.01)
*C07C 231/02* (2006.01)

(52) U.S. Cl.
USPC ........... 564/307; 564/133; 564/134; 564/139; 564/142

(58) Field of Classification Search
None
See application file for complete search history.

(56) References Cited

U.S. PATENT DOCUMENTS

| 5,330,995 | A | 7/1994 | Eicken et al. |
| 5,438,070 | A | 8/1995 | Eicken et al. |
| 5,998,450 | A | 12/1999 | Eicken et al. |
| 6,087,542 | A | 7/2000 | Eicken et al. |
| 8,008,232 | B2 | 8/2011 | Gewehr et al. |
| 2008/0108686 | A1 | 5/2008 | Gewehr et al. |
| 2009/0005597 | A1 | 1/2009 | Smidt et al. |

FOREIGN PATENT DOCUMENTS

| CA | 2 109 470 | 4/1994 |
| EP | 0 545 099 | 6/1993 |
| EP | 0 589 301 | 3/1994 |
| EP | 0 595 150 | 5/1994 |
| GB | 796 951 | 6/1958 |
| GB | 1 512 753 | 6/1978 |
| WO | WO 97 08148 | 3/1997 |
| WO | WO 97/33846 | 9/1997 |
| WO | WO 00 03743 | 1/2000 |
| WO | WO 2004/082677 | 9/2004 |
| WO | WO 2005/123690 | 12/2005 |
| WO | WO 2006/087343 | 8/2006 |
| WO | WO 2007/138089 | 12/2007 |
| WO | WO 2010/094736 | 8/2010 |

OTHER PUBLICATIONS

Albert, J. et al., "Steric and electronic effects on E/Z composition of exocyclic cyclopalladated N-benzylideneamines", Journal of Organometallic Chemistry, (1997), pp. 131-137, vol. 545-546.
Dai, C. et al., "The first general method for palladium-catalyzed negishi cross-coupling of aryl and vinyl chlorides: use of commercially available Pd(P(t-Bu)$_3$)$_2$ as a catalyst", Journal of Am. Chem. Soc., (2001), pp. 2719-2724, vol. 123.
Leardini, R. et al., "A new and convenient synthesis of phenanthridines", Synthesis, (1985), pp. 107-110, vol. 1985, No. 1.
Li, G., "Highly active, air-stable palladium catalysts for the C-C and C-S bond-forming reactions of vinyl and aryl chlorides: use of commercially available [(t-Bu)$_2$P(OH)]$_2$PdCl$_2$,[(t-Bu)$_2$P(OH)PdCl$_2$]$_2$, and [[(t-Bu)2PO***HOP(t_BU)$_2$]PdCl]$_2$ as catalysts", J. Org. Chem., (2002), pp. 3643-3650, vol. 67.
Manolikakes, G. et al., "Palladium- and nickel-catalyzed cross-couplings of unsaturated halides bearing relatively acidic protons with organozinc reagents", J. Org. Chem., (2008), pp. 8422-8436, vol. 73.
Niwa, H., "Studies on the syntheses of diphenyl derivatives (VI) on the amidines", Tohoku Yakka Daigaku Kenkyu Nempo, (1957), pp. 79-89, vol. 4.
Organ, M.G. et al., "A user friendly, all-purpose Pd-NHC (NHC=N-Heterocyclic Carbene) precatalyst for the Negishi reaction: A step towards a universal cross-coupling catalyst", Chem. Eur. J., (2006), pp. 4749-4755, vol. 12.
Xu, H. et al., "Palladium-phosphinous acid-catalyzed cross-coupling of aryl and acyl halides with aryl-, alkyl-, and vinylzinc reagents", J. Org. Chem. (2008), pp. 7638-7650, vol. 73.
Campbell, J. et al., "Facile Palladium-Catalyzed Cross-Coupling of Monoorganozinc Halides with 3-Iodoanthranilonitriles", Synthetic Communications, (1989), pp. 2265-2272, vol. 19.
Jeong, N. et al., "A Facile Preparation of the Fluoroaryl Zinc Halides: an Application to the Synthesis of Diflunisal", Bull. Korean Chem. Soc. (2000), pp. 165-166, vol. 21, No. 2.
Negishi, E. et al., "Selective Carbon-Carbon Bond Formation via Transition Metal Catalysis. 3. [1] A Highly Selective Synthesis of Unsymmetrical Biaryls and Diarylmethanes by the Nickel- or Palladium- Catalyzed Reaction of Aryl- and Benzylzinc Derivatives with Aryl Halides", J. Org. Chem., (1977), pp. 1821-1823, vol. 42, No. 10.
Allan, Zdenek et al., "Aromatic Diazo Compounds XIV. The Phenylation of p-Phenylenediamine in the Nucleus and the Corresponding Reaction Mechanism", Chemicke Listy, 1953, pp. 52-60, vol. 47, Research Inst., Pardubice-Rybitvi, Czech.

(Continued)

*Primary Examiner* — Brian J Davis
(74) *Attorney, Agent, or Firm* — Brinks Gilson & Lione

(57) ABSTRACT

The present invention relates to a process for preparing substituted 2-aminobiphenyls and to a process for preparing (Het)arylamides of such 2-aminobiphenyls.

26 Claims, No Drawings

(56) References Cited

OTHER PUBLICATIONS

Allan, Zdenek et al, "Aromatic Diazo Compounds VIII Coupling with Benzidine", Chemicke Listy, 1952, pp. 485-486, vol. 46, Research Inst., Pardubice-Rybitvi, Czech. (XP 002504740).

Hollingsworth, B.L. et al, "Some α ω-Di(phenanthridin-6-yl) alkanes", Journal of the Chemical Society, 1961, p. 3664-3667.

Jensen, Anne et al., "Preparation of 2-arylated-1,4-phenylenediamines by palladium-catalyzed cross-coupling reactions", Journal of Organometallic Chemistry, Jul. 1, 2002, pp. 122-128, vol. 653, No. 1-2, Elsevier-Sequoia S.A. Lausanne, CH.

Wetzel, Alexander et al., "Synthesis of amino-and hydroxybiphenyls by radical chain reaction of arenediazonium salts", Angewandte Chemie, International Edition, 2008, pp. 9130-9133, vol. 47.

METHOD FOR PRODUCING AMINOBIPHENYLENE

This application is a National Stage application of International Application No. PCT/EP2009/058457, filed Jul. 3, 2009, the entire contents of which is hereby incorporated herein by reference. This application also claims priority under 35 U.S.C. §119 to European Patent Application No. 08159632.2, filed Jul. 3, 2008 and European Patent Application No. 08166713.1, filed Oct. 15, 2008, the entire contents of which are hereby incorporated herein by reference.

The present invention relates to a process for preparing substituted aminobiphenyls, especially 2-aminobiphenyls and to a process for preparing (het)arylamides of such aminobiphenyl, especially 2-aminobiphenyls.

Functionalized biphenyl compounds are of great interest especially as pharmaceuticals and pesticides, and as precursors of such active ingredients. For their synthesis, a series of organometallic methods is available, which offer efficient access to a multitude of biphenyl derivatives. However, organometallic methods are also afflicted by some disadvantages. For instance, their attractiveness is reduced by high costs, especially in the case of palladium-catalyzed reactions, lack of environmental compatibility, as in the case of nickel, and low maturity, especially in the case of catalysis with cobalt and iron compounds. In comparison to organometallic methods, processes based on the addition of aryl radicals onto aryl compounds have gained little attention specifically in the recent past.

Ring-substituted 2-aminobiphenyls are important precursors for aryl- and hetarylcarboxamides which find use as fungicides, and for which boscalid is a prominent representative.

Addition reactions of aryl radicals onto aniline derivatives have been known for some time. For instance, Allan and Muzik (Chem. Abstr. 1953, 8705) describe reactions of the diazonium salt of para-nitrophenylamine with benzidine and N,N,N',N'-tetramethyl-benzidine. While the tetramethyl derivative enters into free-radical biaryl coupling, the unsubstituted benzidine, however, reacts by a non-free-radical mechanism to give the corresponding triazene. A disadvantage of the known free-radical biaryl couplings is that they usually proceed with low selectivity. Allan and Muzik also describe, in Chemické listy 47, 1801 (1953), the coupling of benzenediazonium salts with electron-withdrawing substitution to p-phenylenediamine. This forms exclusively polyarylated phenylenediamines; selective monoarylation is not achieved.

It was an object of the present invention to provide easily performable processes for preparing ring-substituted aminobiphenyls, especially 2-aminobiphenyls, and for preparing (het)arylcarboxamides derived therefrom. These processes should additionally be performable inexpensively and be based on selective conversions.

The object is achieved by the processes described in detail below.

The present invention provides a process for preparing aminobiphenyls of the general formula (I)

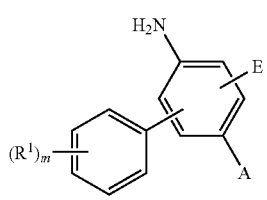

in which m is 0, 1, 2 or 3;

each $R^1$ is independently halogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, nitro, cyano, $SO_3R^3$, $SO_2R^3$, $SO_2NR^{10}R^{11}$, $COOR^2$, $COR^4$, $OCOR^4$, $CONR^{10}R^{11}$, $NR^{10}COR^4$, $NR^{10}SO_2R^3$, $C_1$-$C_4$-alkylimino, aryl, aryloxy, arylcarbonyl, arylmethoxycarbonyl, arylalkylimino or 5- or 6-membered hetaryl having 1, 2 or 3 heteroatoms selected from N, O und S, as ring members, where the aryl group and the hetaryl group in the 7 latter radicals optionally bear 1, 2, 3, or 4 substituents which are selected from halogen, $C_1$-$C_4$-alkyl, $C_1$-$C_4$-haloalkyl, $C_1$-$C_4$-alkoxy and $C_1$-$C_4$-haloalkoxy;

A is hydrogen, $NR^5R^6$, $(NR^7R^8R^9)^+V^-$, halogen, $C_1$-$C_4$-alkyl, alkoxy, $C_1$-$C_4$-haloalkoxy, $C_1$-$C_4$-alkylcarbonyl, $C_1$-$C_4$-haloalkylcarbonyl, nitro, hydroxyl, $SO_3R^3$, $COOR^2$, $CONR^{10}R^{11}$, $COR^4$, aryl or aryloxy, where the aryl group in the two latter radicals optionally bears 1, 2, 3 or 4 substituents which are selected from halogen, $C_1$-$C_4$-alkyl, $C_1$-$C_4$-haloalkyl, $C_1$-$C_4$-alkoxy and $C_1$-$C_4$-haloalkoxy; and E is hydrogen, halogen, $C_1$-$C_4$-alkyl, $C_1$-$C_4$-haloalkyl, $C_1$-$C_4$-hydroxyalkyl, $C_3$-$C_6$-cycloalkyl, aryl or 5- or 6-membered hetaryl having 1, 2 or 3 heteroatoms which are selected from N, O and S as ring members, where the aryl and the hetaryl group optionally bear 1, 2, 3, 4 or 5 substituents which are selected from halogen, $C_1$-$C_4$-alkyl, $C_1$-$C_4$-haloalkyl, $C_1$-$C_4$-alkoxy and $C_1$-$C_4$-haloalkoxy;

in which each $R^2$ is independently hydrogen, $C_1$-$C_4$-alkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from N, O und S as ring members or a cation equivalent;

$R^3$ is hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from N, O and S as ring members;

$R^4$ is hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from N, O and S as ring members;

$R^5$ and $R^6$ are each independently hydrogen, $C_1$-$C_{10}$-alkyl, $C_3$-$C_4$-alkenyl, $C_3$-$C_{10}$-cycloalkyl, $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocarbonyl, di-($C_1$-$C_4$-alkyl)aminocarbonyl, $C_1$-$C_4$-alkylsulfonyl, $C_1$-$C_4$-haloalkylsulfonyl, aryl, aryl-$C_1$-$C_4$-alkyl, arylcarbonyl, aryloxycarbonyl or arylmethoxycarbonyl, where the aryl groups of the latter five substituents optionally each bear 1, 2, 3 or 4 substituents which are selected from halogen, nitro, $C_1$-$C_4$-alkyl, $C_1$-$C_4$-haloalkyl, $C_1$-$C_4$-alkoxy and $C_1$-$C_4$-haloalkoxy; or $R^5$ and $R^6$ together form a =$CR^{12}$—$NR^{13}R^{14}$ group or, together with the nitrogen atom to which they are bonded, form a $C_1$-$C_4$-alkylimino group or an aryl-$C_1$-$C_4$-alkylimino group;

$R^7$, $R^8$ and $R^9$ are each independently $C_1$-$C_{10}$-alkyl;

$R^{10}$ and $R^{11}$ are each independently hydrogen, $C_1$-$C_{10}$-alkyl, hydroxyalkyl, $C_3$-$C_4$-alkenyl, $C_3$-$C_4$-alkynyl, $C_3$-$C_{10}$-cycloalkyl, $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylsulfonyl, $C_1$-$C_4$-haloalkylsulfonyl, aryl, aryl-$C_1$-$C_4$-alkyl, arylcarbonyl, aryloxycarbonyl, aryl methoxycarbonyl or 5- or 6- membered hetaryl having 1, 2 or 3 heteroatoms selected from N, O and S as ring members, where the aryl and hetaryl groups of the latter 6 substituents optionally each bear 1, 2, 3 or 4 substituents which are selected from halogen, nitro, $C_1$-$C_4$-alkyl, $C_1$-$C_4$-alkoxy and $C_1$-$C_4$-haloalkoxy;

$R^{12}R^{13}$ and $R^{14}$ are each independently hydrogen, $C_1$-$C_{10}$-alkyl or aryl; and $V^-$ denotes a monovalent anion or the portion of a polyvalent anion equivalent to a monovalent anion;

comprising the following steps:

(i) reacting a diazonium salt of the formula (II) with an aniline derivative of the formula (III)

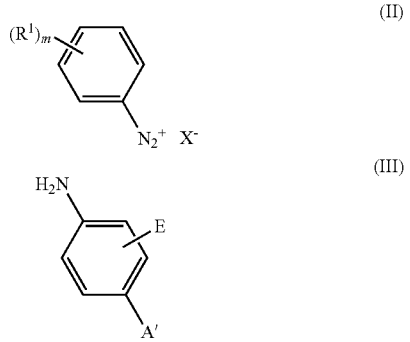

in which

A' is as defined for A, with the proviso that A' is not hydrogen;

$X^-$ is a monovalent anion or the portion of a polyvalent anion equivalent to a monovalent anion; and m, E and $R^1$ are each as defined above, under reaction conditions which can bring about decomposition of the diazonium salt of the formula II to nitrogen and an aryl radical, to obtain an aminobiphenyl of the formula (I')

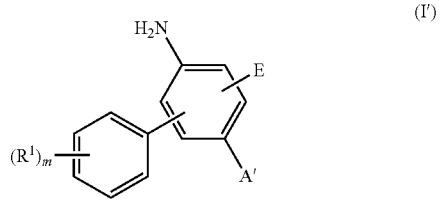

and (ii) optionally converting the aminobiphenyl of the formula (I') obtained in step (i) to an aminobiphenyl of the formula (I) in which A is hydrogen.

This process is referred to hereinafter as process A.

In the context of the present invention, the terms used generically are defined as follows:

The prefix $C_x$-$C_y$ denotes the number of possible carbon atoms in the particular case.

The term "halogen" denotes in each case fluorine, bromine, chlorine or iodine, especially fluorine, chlorine or bromine.

The term "$C_1$-$C_4$-alkyl" denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term "$C_1$-$C_{10}$-alkyl" denotes a linear or branched alkyl radical comprising from 1 to 10 carbon atoms. Examples are, as well as the radicals specified for $C_1$-$C_4$-alkyl, pentyl, hexyl, heptyl, octyl, 2-ethylhexyl, nonyl, decyl, 2-propylheptyl and positional isomers thereof.

The term "$C_1$-$C_4$-haloalkyl", as used herein and in the haloalkyl units of $C_1$-$C_4$-haloalkoxy, describes straight-chain or branched alkyl groups having from 1 to 4 carbon atoms, where some or all of the hydrogen atoms of these groups have been replaced by halogen atoms. Examples thereof are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3,3,3-trifluoroprop-1-yl, 1,1,1-trifluoroprop-2-yl, 3,3,3-trichloroprop-1-yl, heptafluoroisopropyl, 1-chlorobutyl, 2-chlorobutyl, 3-chlorobutyl, 4-chlorobutyl, 1-fluorobutyl, 2-fluoro-butyl, 3-fluorobutyl, 4-fluorobutyl and the like.

The term "$C_1$-$C_4$-hydroxyalkyl" describes straight-chain or branched alkyl groups having 1 to 4 carbon atoms, where one hydrogen atom in these groups is replaced by an OH group. Examples are hydroxymethyl, 1- and 2-hydroxyethyl, 1-, 2- and 3-hydroxypropyl, 1-, 2- and 3-hydroxyprop-2-yl, 1-, 2-, 3- and 4-hydroxybutyl and positional isomers thereof.

The term "$C_3$-$C_4$-alkenyl" denotes a monounsaturated linear or branched aliphatic radical having 3 or 4 carbon atoms. Examples thereof are propen-1-yl, propen-2-yl (allyl), but-1-en-1-yl, but-1-en-2-yl, but-1-en-3-yl, but-1-en-4-yl, but-2-en-1-yl, but-2-en-2-yl, but-2-en-4-yl, 2-methylprop-1-en-1-yl, 2-methylprop-2-en-1-yl and the like.

The term "$C_3$-$C_4$-alkynyl" denotes a linear or branched aliphatic radical having a triple bond and 3 or 4 carbon atoms. Examples thereof are propyn-1-yl, propargyl and butinyl.

The term "$C_2$-$C_4$-alkynyl" denotes a linear or branched aliphatic radical having a triple bond and 2, 3 or 4 carbon atoms. Examples thereof are ethinyl, propyn-1-yl, propargyl and butinyl.

The term "$C_3$-$C_6$-cycloalkyl" denotes a saturated alicyclic radical having from 3 to 6 carbon atoms as ring members. Examples are cyclopropyl, cyclobutyl, cyclopentyl and cyclohexyl. The cycloalkyl radicals may bear 1, 2 or 3 substituents which are selected from $C_1$-$C_4$-alkyl and halogen.

The term "$C_3$-$C_{10}$-cycloalkyl" denotes a saturated alicyclic radical having from 3 to 10 carbon atoms as ring members. Examples are cyclopropyl, cyclobutyl, cyclopentyl, cyclohexyl, cycloheptyl, cyclooctyl, cyclononyl and cyclodecyl. The cycloalkyl radicals may bear 1, 2 or 3 substituents which are selected from $C_1$-$C_4$-alkyl and halogen.

The term "$C_1$-$C_4$-alkoxy" denotes straight-chain or branched saturated alkyl groups comprising from 1 to 4 carbon atoms, which are bonded via an oxygen atom. Examples of $C_1$-$C_4$-alkoxy are methoxy, ethoxy, n-propoxy, 1-methylethoxy (isopropoxy), n-butoxy, 1-methylpropoxy (sec-butoxy), 2-methylpropoxy (isobutoxy) and 1,1-dimethylethoxy (tert-butoxy).

The term "$C_1$-$C_4$-haloalkoxy" describes straight-chain or branched saturated haloalkyl groups comprising from 1 to 4 carbon atoms, which are bonded via an oxygen atom. Examples thereof are chloromethoxy, bromomethoxy, dichloromethoxy, trichloro-methoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, 1,1,2,2-tetrafluoroethoxy, 1-chloro-1,2,2-trifluoroethoxy, pentafluoroethoxy, 3,3,3-trifluoroprop-1-oxy, 1,1,1-trifluoroprop-2-oxy, 3,3,3-trichloroprop-1-oxy, 1-chloro-butoxy, 2-chlorobutoxy, 3-chlorobutoxy, 4-chlorobutoxy, 1-fluorobutoxy, 2-fluorobutoxy, 3-fluorobutoxy, 4-fluorobutoxy and the like.

The term "$C_1$-$C_4$-alkylthio" denotes straight-chain or branched saturated alkyl groups comprising 1 to 4 carbon atoms, which are bonded via a sulfur atom. Examples of $C_1$-$C_4$-alkylthio are methylthio, ethylthio, n-propylthio, 1-methylethylthio (isopropylthio), n-butylthio, 1-methylpropylthio (sec-butylthio), 2-methylpropylthio (isobutylthio) and 1,1-dimethylethylthio (tert-butylthio).

The term "$C_1$-$C_4$-haloalkylthio" describes straight-chain or branched saturated haloalkyl groups comprising 1 to 4 carbon atoms, which are bonded via a sulfur atom. Examples thereof are chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, 1,1,2,2-tetrafluoroethylthio, 1-chloro-1,2,2-trifluoroethylthio, pentafluoroethylthio, 3,3,3-trifluoroprop-1-ylthio, 1,1,1-trifluoroprop-2-ylthio, 3,3,3-trichloroprop-1-ylthio, 1-chlorobutylthio, 2-chlorobutylthio, 3-chlorobutylthio, 4-chlorobutylthio, 1-fluorobutylthio, 2-fluorobutylthio, 3-fluorobutylthio, 4-fluorobutylthio and the like.

The term "$C_1$-$C_4$-alkylcarbonyl" denotes alkyl radicals having from 1 to 4 carbon atoms which are bonded via a carbonyl group. Examples thereof are methylcarbonyl (acetyl), ethylcarbonyl, propylcarbonyl, isopropylcarbonyl, n-butylcarbonyl, sec-butylcarbonyl, isobutylcarbonyl and tert-butylcarbonyl.

The term "$C_1$-$C_4$-haloalkylcarbonyl" denotes haloalkyl radicals having from 1 to 4 carbon atoms which are bonded via a carbonyl group. Examples thereof are fluoro-methylcarbonyl, difluoromethylcarbonyl, trifluoromethylcarbonyl, 1-fluoroethylcarbonyl, 2-fluoroethylcarbonyl, 1,1-difluoroethylcarbonyl, 2,2-difluoroethylcarbonyl, 2,2,2-tri-fluoroethylcarbonyl, pentafluoroethylcarbonyl and the like.

The term "$C_3$-$C_4$-alkenylcarbonyl" denotes alkenyl radicals having 3 or 4 carbon atoms which are bonded via a carbonyl group. Examples thereof are propen-1-ylcarbonyl, propen-2-ylcarbonyl (allylcarbonyl), but-1-en-1-ylcarbonyl, but-1-en-2-ylcarbonyl, but-1-en-3-ylcarbonyl, but-1-en-4-ylcarbonyl, but-2-en-1-ylcarbonyl, but-2-en-2-ylcarbonyl, but-2-en-4-ylcarbonyl, 2-methylprop-1-en-1-ylcarbonyl, 2-methylprop-2-en-1-ylcarbonyl and the like.

The term "$C_1$-$C_4$-alkoxycarbonyl" denotes alkoxy radicals having from 1 to 4 carbon atoms which are bonded via a carbonyl group. Examples thereof are methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl.

The term "$C_1$-$C_4$-haloalkoxycarbonyl" denotes haloalkoxy radicals having from 1 to 4 carbon atoms which are bonded via a carbonyl group. Examples thereof are fluoro-methoxycarbonyl, difluoromethoxycarbonyl, trifluoromethoxycarbonyl, 1-fluoroethoxy-carbonyl, 2-fluoroethoxycarbonyl, 1,1-difluoroethoxycarbonyl, 2,2-difluoroethoxy-carbonyl, 2,2,2-trifluoroethoxycarbonyl, pentafluoroethoxycarbonyl and the like.

The term "$C_3$-$C_4$-alkenyloxycarbonyl" denotes alkenyloxy radicals having 3 or 4 carbon atoms which are bonded via a carbonyl group. Examples thereof are allyloxycarbonyl and methallyloxycarbonyl.

The term "$C_1$-$C_4$-alkylsulfonyl" denotes alkyl radicals having from 1 to 4 carbon atoms which are bonded via a sulfonyl group ($SO_2$). Examples thereof are methylsulfonyl, ethylsulfonyl, propylsulfonyl, isopropylsulfonyl, n-butylsulfonyl, sec-butylsulfonyl, isobutylsulfonyl and tert-butylsulfonyl.

The term "$C_1$-$C_4$-haloalkylsulfonyl" denotes haloalkyl radicals having from 1 to 4 carbon atoms which are bonded via a sulfonyl group ($SO_2$). Examples thereof are fluoromethyl-sulfonyl, difluoromethylsulfonyl, trifluoromethylsulfonyl, 1-fluoroethylsulfonyl, 2-fluoro-ethylsulfonyl, 1,1-difluoroethylsulfonyl, 2,2-difluoroethylsulfonyl, 2,2,2-trifluoroethyl-sulfonyl, pentafluoroethylsulfonyl and the like.

The term "aryl" denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

The term "hetaryl" denotes aromatic radicals having from 1 to 3 heteroatoms which are selected from O, N and S. Examples thereof are 5- and 6-membered hetaryl radicals having 1, 2 or 3 heteroatoms selected from O, S and N as ring members, such as pyrrolyl, furanyl, thienyl, pyrazolyl, imidazolyl, oxazolyl, isoxazolyl, thiazolyl, isothiazolyl, triazolyl, pyridyl, pyrazinyl, pyridazinyl, pyrimidyl and triazinyl.

The term "arylcarbonyl" denotes aryl radicals which are bonded via a carbonyl group. Examples thereof are phenylcarbonyl and naphthylcarbonyl.

The term "aryl-$C_1$-$C_4$-alkyl" denotes aryl radicals which are bonded via a $C_1$-$C_4$-alkyl group. Examples thereof are benzyl, 2-phenylethyl (phenethyl) and the like.

The term "arylmethoxycarbonyl" denotes arylmethoxy radicals which are bonded via a carbonyl group. Examples thereof are benzyloxycarbonyl and fluorenylmethoxy-carbonyl.

The term "$C_1$-$C_4$-alkylimino" denotes a radical of the formula —N=R in which R is $C_1$-$C_4$-alkylene such as $CH_2$, $CHCH_3$, $CHCH_2CH_3$, $C(CH_3)_2$, $CHCH_2CH_2CH_3$, $C(CH_3)CH_2CH_3$ or $CHCH(CH_3)_2$.

The term "aryl-$C_1$-$C_4$-alkylimino" denotes a radical of the formula —N=R in which R is aryl-$C_1$-$C_4$-alkylene such as benzylidene (R=CH-phenyl).

The remarks made below regarding preferred configurations of the processes according to the invention, especially regarding preferred configurations of the radicals of the different reactants and products and of the reaction conditions of the processes according to the invention, apply either taken alone or, more particularly, in any conceivable combination with one another.

The reactions described herein are carried out in reaction vessels customary for such reactions, the reaction being configurable continuously, semicontinuously or batchwise. In general, the particular reactions will be performed under atmospheric pressure.

However, the reactions can also be performed under reduced (e.g. 0.1 to 1 bar) or elevated (e.g. 1.1 to 10 bar) pressure.

In the compounds of the formulae (I) and (II), m is preferably 1, 2 or 3. When m is 1, $R^1$ is preferably in the para or meta position to the diazonium substituents.

In the compounds of the formulae (I) and (II), $R^1$ is preferably halogen, $C_1$-$C_4$-alkyl, $C_1$-$C_4$-haloalkyl, $C_1$-$C_4$-alkoxy, $C_1$-$C_4$-haloalkoxy, nitro, cyano or optionally halogen-, $C_1$-$C_4$-alkyl- or $C_1$-$C_4$-alkoxy-substituted aryloxy. $R^1$ is more preferably halogen, $C_1$-$C_4$-alkoxy, $C_1$-$C_4$-haloalkoxy or optionally halogen-, $C_1$-$C_4$-alkyl- or $C_1$-$C_4$-alkoxy-substituted aryloxy, even more preferably halogen, $C_1$-$C_4$-alkyl, $C_1$-$C_4$-alkoxy, $C_1$-$C_4$-haloalkoxy, cyano or optionally halogen-, $C_1$-$C_4$-alkyl- or $C_1$-$C_4$-alkoxy-substituted aryloxy, and even further preferably chlorine, bromine, fluorine, $C_1$-$C_2$-alkoxy or phenoxy. More particularly, $R^1$ is 2-F, 3-F, 4-F, 2-Cl, 3-Cl, 4-Cl, 2-Br, 3-Br, 4-Br, 2-methyl, 3-methyl, 4-methyl, 2-trifluoromethyl, 3-trifluoromethyl, 4-trifluoromethyl, 2-methoxy, 3-methoxy, 4-methoxy, 2-trifluoromethoxy, 3-trifluoromethoxy, 4-trifluoromethoxy, 2-phenoxy, 3-phenoxy, 4-phenoxy, 3,4-$F_2$, 3,4-$Cl_2$, 2,3,4-$F_3$, 3,4,5-$F_3$ or 3,4,5-$Cl_3$, and especially 2-F, 4-F, 2-Cl, 4-Cl, 2-Br, 4-Br, 2-methoxy, 4-methoxy, 2-phenoxy, 4-phenoxy, 3,4-$F_2$, 3,4-$Cl_2$, 2,3,4-$F_3$, 3,4,5-$F_3$ or 3,4,5-$Cl_3$. The statement of position relates to the 1-position through which the aryl radical deriving from the compound of the formula (II) is bonded to the aniline ring (i.e. to the radical which derives from the compound of the formula (III), or to the 1-position of the diazonium radical in the diazonium salt II.

In the definition of A and A', $V^-$ is preferably a halide, such as chloride, bromide or iodide, $BF_4^-$, $PF_6^-$, $\frac{1}{2}SO_4^{2-}$ or acetate. $V^-$ is more preferably a halide, such as chloride, bromide or iodide, $BF_4^-$ or $\frac{1}{2}SO_4^{2-}$.

In the definition of A, A' and $R^1$, $R^2$ is preferably hydrogen or $C_1$-$C_4$-alkyl.

In the definition of A, A' and $R^1$, $R^3$ is preferably hydrogen or $C_1$-$C_4$-alkyl.

In the definition of A, A' and $R^1$, $R^4$ is preferably hydrogen or $C_1$-$C_4$-alkyl, and especially In the definition of A and A', $R^5$ and $R^6$ are each independently preferably hydrogen, $C_1$-$C_{10}$-alkyl, $C_3$-$C_4$-alkenyl, $C_1$-$C_{10}$-alkylcarbonyl, $C_1$-$C_4$-alkoxycarbonyl, $C_3$-$C_4$-alkenyloxycarbonyl, $C_1$-$C_{10}$-alkylsulfonyl, aryl, aryl-$C_1$-$C_2$-alkyl, aryloxycarbonyl or arylalkoxy-carbonyl, where the aryl group in the latter four radicals may also bear 1, 2 or 3 substituents which are selected from halogen, $C_1$-$C_4$-alkyl and $C_1$-$C_4$-alkoxy, or they together form a =$CR^{12}$—$NR^{13}R^{14}$ group in which $R^{12}$ is preferably H and $R^{13}$ and $R^{14}$ are preferably each methyl, or, together with the nitrogen atom to which they are bonded, they form a $C_1$-$C_4$-alkylimino group or a benzylimino group. More preferably, $R^5$ and $R^6$ are each independently hydrogen, $C_3$-$C_4$-alkenyl (especially allyl), $C_1$-$C_4$-alkoxycarbonyl, $C_3$-$C_4$-alkenyloxycarbonyl, benzyl, methylbenzyl, e.g. 2-methylbenzyl, 3-methylbenzyl or 4-methylbenzyl, methoxybenzyl, e.g. 2-methoxybenzyl, 3-methoxy-benzyl or 4-methoxybenzyl, benzyloxycarbonyl or fluorenylmethoxycarbonyl, even more preferably hydrogen, $C_3$-$C_4$-alkenyl, in particular allyl, $C_1$-$C_4$-alkoxycarbonyl, in particular tert-butoxycarbonyl, allyloxycarbonyl, benzyl, methylbenzyl, e.g. 2-methyl-benzyl, 3-methylbenzyl or 4-methylbenzyl, methoxybenzyl, e.g. 2-methoxybenzyl, 3-methoxybenzyl or 4-methoxybenzyl, benzyloxycarbonyl or fluorenylmethoxycarbonyl, and especially hydrogen or $C_1$-$C_4$-alkoxycarbonyl, in particular tert-butoxycarbonyl. Preferably, one of the $R^5$ and $R^6$ radicals is hydrogen and the other has one of the definitions specified above. The tert-butoxycarbonyl radical is also referred to as Boc. Alternatively, $R^5$ and $R^6$ are preferably both allyl. Alternatively, $R^5$ and $R^6$ together preferably form a =$CR^{12}$—$NR^{13}R^{14}$ group in which $R^{12}$ is preferably H and $R^{13}$ and $R^{14}$ are preferably each methyl, or, together with the nitrogen atom to which they are bonded, they form a $C_1$-$C_4$-alkylimino group or a benzylimino group. Specific definitions for particular process variants are each defined at the appropriate point.

In the compound of the formula (I), A is preferably hydrogen, bromine, chlorine, fluorine, $C_1$-$C_4$-alkoxy, nitro, $C_1$-$C_4$-alkylcarbonyl, $C_1$-$C_4$-alkoxycarbonyl or $NR^5R^6$. More preferably, A is hydrogen, bromine, chlorine, fluorine, $C_1$-$C_4$-alkoxy, nitro, $C_1$-$C_4$-alkyl-carbonyl, $C_1$-$C_4$-alkoxycarbonyl or $NR^5R^6$. In particular, A is hydrogen, bromine, chlorine, fluorine, $C_1$-$C_4$-alkoxy, $C_1$-$C_4$-alkylcarbonyl, $C_1$-$C_4$-alkoxycarbonyl or $NR^5R^6$. A is especially hydrogen, $C_1$-$C_4$-alkoxy, $C_1$-$C_4$-alkylcarbonyl, $C_1$-$C_4$-alkoxycarbonyl or $NR^5R^6$.

$R^5$ is preferably hydrogen and $R^6$ is preferably selected from hydrogen, $C_3$-$C_4$-alkenyl, $C_1$-$C_{10}$-alkylcarbonyl, $C_1$-$C_4$-alkoxycarbonyl, $C_3$-$C_4$-alkenyloxycarbonyl, aryloxycarbonyl and arylalkoxycarbonyl, where the aryl group in the three aforementioned radicals may also bear 1, 2 or 3 substituents which are selected from halogen, $C_1$-$C_4$-alkyl and $C_1$-$C_4$-alkoxy; more preferably from hydrogen, $C_3$-$C_4$-alkenyl (especially allyl), $C_1$-$C_4$-alkoxycarbonyl, $C_3$-$C_4$-alkenyloxycarbonyl, benzyl, methylbenzyl, e.g. 2-methylbenzyl, 3-methylbenzyl or 4-methyl benzyl, methoxy-benzyl, e.g. 2-methoxybenzyl, 3-methoxybenzyl or 4-methoxybenzyl, benzyloxy-carbonyl and fluorenylmethoxycarbonyl, and especially from hydrogen, $C_3$-$C_4$-alkenyl, in particular allyl, $C_1$-$C_4$-alkoxycarbonyl, in particular tert-butoxycarbonyl, allyloxy-carbonyl, benzyl, benzyloxycarbonyl, fluorenyl-methoxycarbonyl and methoxybenzyl. $R^6$ is especially hydrogen or $C_1$-$C_4$-alkoxycarbonyl and more especially hydrogen or tert-butoxycarbonyl. Alternatively, $R^5$ and $R^6$ are preferably both allyl. Alternatively, $R^5$ and $R^6$ preferably together form a =$CR^{12}$—$NR^{13}R^{14}$ group in which $R^{12}$ is preferably H and $R^{13}$ and $R^{14}$ are preferably each methyl, or, together with the nitrogen atom to which they are bonded, they form a $C_1$-$C_4$-alkylimino group or a benzylimino group.

In the compound of the formula (III), A' is preferably bromine, chlorine, fluorine, $C_1$-$C_4$-alkoxy, nitro, $C_1$-$C_4$-alkylcarbonyl, $C_1$-$C_4$-alkoxycarbonyl or $NR^5R^6$. More preferably, A' is bromine, chlorine, fluorine, $C_1$-$C_4$-alkoxy, nitro, $C_1$-$C_4$-alkylcarbonyl, $C_1$-$C_4$-alkoxy-carbonyl or $NR^5R^6$. In particular, A' is bromine, chlorine, fluorine, $C_1$-$C_4$-alkoxy, $C_1$-$C_4$-alkylcarbonyl, $C_1$-$C_4$-alkoxycarbonyl or $NR^5R^6$. A' is especially $C_1$-$C_4$-alkoxy, $C_1$-$C_4$-alkylcarbonyl, $C_1$-$C_4$-alkoxycarbonyl or $NR^5R^6$.

$R^5$ is preferably hydrogen and $R^6$ is preferably selected from hydrogen, $C_3$-$C_4$-alkenyl, $C_1$-$C_{10}$-alkylcarbonyl, $C_1$-$C_4$-alkoxycarbonyl, $C_3$-$C_4$-alkenyloxycarbonyl, aryl-$C_1$-$C_2$-alkyl, aryloxycarbonyl and arylalkoxycarbonyl, where the aryl group in the three aforementioned radicals may also bear 1, 2 or 3 substituents which are selected from halogen, $C_1$-$C_4$-alkyl and $C_1$-$C_4$-alkoxy; more preferably from hydrogen, $C_3$-$C_4$-alkenyl (especially allyl), $C_1$-$C_4$-alkoxycarbonyl, $C_3$-$C_4$-alkenyloxycarbonyl, benzyl, methylbenzyl, e.g. 2-methylbenzyl, 3-methylbenzyl or 4-methylbenzyl, methoxy-benzyl, e.g. 2-methoxybenzyl, 3-methoxybenzyl or 4-methoxybenzyl, benzyloxy-carbonyl and fluorenylmethoxycarbonyl, and especially from hydrogen, $C_3$-$C_4$-alkenyl, in particular allyl, $C_1$-$C_4$-alkoxycarbonyl, in particular tert-butoxycarbonyl, allyloxy-carbonyl, benzyl, benzyloxycarbonyl, fluorenylmethoxycarbonyl and methoxybenzyl. $R^6$ is especially hydrogen or $C_1$-$C_4$-alkoxycarbonyl and more especially hydrogen or tert-butoxycarbonyl. Alternatively, $R^5$ and $R^6$ are preferably both allyl. Alternatively, $R^5$ and $R^6$ preferably together form a =$CR^{12}$—$NR^{13}R^{14}$ group in which $R^{12}$ is preferably H and $R^{13}$ and $R^{14}$ are preferably each methyl, or, together with the nitrogen atom to which they are bonded, they form a $C_1$-$C_4$-alkylimino group or a benzylimino group.

E is preferably hydrogen, halogen, $C_1$-$C_4$-alkyl, $C_1$-$C_4$-haloalkyl, $C_1$-$C_4$-hydroxyalkyl or $C_3$-$C_6$-cycloalkyl. $R^3$ is more preferably hydrogen, halogen or $C_1$-$C_4$-alkyl and especially hydrogen.

In the compound of the formula (II), $X^-$ is preferably a halide, such as chloride or bromide, $BF_4^-$, $PF_6^-$, $SbF_6^-$, ½ $SO_4^{2-}$, acetate, trifluoroacetate, trichloroacetate, the anion of an aromatic 1,2-dicarboximide or the anion of an aromatic 1,2-disulfonimide. In the latter two cases, the anion forms through abstraction of the proton on the imide nitrogen atom. Examples of anions of aromatic 1,2-dicarboximides are the anion of phthalimide, where the phenyl ring of the phthalimide may bear 1, 2, 3 or 4 substituents which are selected from halogen, OH, $C_1$-$C_4$-alkyl, $C_1$-$C_4$-haloalkyl, $C_1$-$C_4$-alkoxy and $C_1$-$C_4$-haloalkoxy, and the anion of naphthalene-1,2-dicarboximide or of naphthalene-2,3-dicarboximide, where the naphthyl ring of the naphthalenedicarboximide may bear 1, 2, 3 or 4 substituents which are selected from halogen, OH, $C_1$-$C_4$-alkyl, haloalkyl, $C_1$-$C_4$-alkoxy and $C_1$-$C_4$-haloalkoxy. Examples of anions of aromatic 1,2-disulfonimides are the anion of ortho-benzenesulfonimide, where the phenyl ring of the benzenedisulfonimide may bear 1, 2, 3 or 4 substituents which are selected from halogen, OH, $C_1$-$C_4$-alkyl, $C_1$-$C_4$-haloalkyl, $C_1$-$C_4$-alkoxy and $C_1$-$C_4$-haloalkoxy, and the anion of naphthalene-1,2-disulfonimide or of naphthalene-2,3-disulfonimide, where the naphthyl ring of the naphthalenedisulfonimide may bear 1, 2, 3 or 4 substituents which are selected from halogen, OH, $C_1$-$C_4$-alkyl, $C_1$-$C_4$-haloalkyl, $C_1$-$C_4$-alkoxy and $C_1$-$C_4$-haloalkoxy. $X^-$ is more preferably a halide, such as chloride or bromide, $BF_4^-$, $PF_6^-$, ½ $SO_4^{2-}$, acetate or the anion of an aromatic 1,2-sulfonic diimide, such as especially ortho-benzenedisulfonimide. In particular, $X^-$ is $BF_4^-$ or chloride.

The inventive reaction is effected by contacting the starting compounds, i.e. a diazonium salt of the formula (II) and an aniline derivative of the formula (III), preferably in a suitable solvent, with one another under reaction conditions which bring about decomposition of the diazonium salt of the formula II to nitrogen and an aryl radical.

The reactants can in principle be contacted with one another in different sequences. For example, the aniline of the formula III, optionally dissolved or dispersed in a solvent (mixture), can be initially charged and admixed with the diazonium salt II, or, conversely, the diazonium salt, optionally dissolved or dispersed in a solvent (mixture), can be initially charged and admixed with the aniline of the formula III. However, it has generally been found to be advantageous to initially charge the aniline of the formula III, optionally in a solvent (mixture), and to add the diazonium salt II thereto.

The reaction in step (i) can be carried out either in a solvent or in bulk. In the latter case, for example, the aniline III itself functions as a solvent or dispersant or is, if its boiling point is above room temperature (25° C.), initially charged as the melt and then admixed with the diazonium salt II under suitable reaction conditions. However, preference is given to performance in a solvent.

Suitable solvents depend specifically on the selection of the particular reaction conditions for the decomposition of the diazonium salt II, for example the reactants. However, it has generally been found to be favorable to use an aqueous solvent as the solvent for the reaction of compounds (II) and (III).

In the processes according to the invention, aqueous solvents are understood to mean water or mixtures of water with water-miscible organic solvents. Examples of useful organic solvents here include short-chain nitriles such as acetonitrile or propionitrile, amides such as dimethylformamide, short-chain mono- or polyhydric alcohols such as methanol, ethanol, propanol, isopropanol, ethylene glycol or trifluoroethanol, short-chain carboxylic acids such as glacial acetic acid/acetic acid, and short-chain ketones such as acetone, or mixtures of these organic solvents with one another.

Aqueous solvents in the context of the present invention are also aqueous acid solutions, especially aqueous mineral acids, such as hydrochloric acid, hydrobromic acid, nitric acid, sulfuric acid, phosphoric acid and the like. Among these, preference is given to nonoxidizing acids such as hydrochloric acid or hydrobromic acid. In a preferred embodiment, the acid solutions are used in dilute form. In this connection, "dilute" means that the concentration of the acid is from 0.1 to 20% by weight, in particular from 3 to 15% by weight and especially from 2 to 8% by weight, based on the weight of the solvent. The aqueous acid solutions can also be used in a mixture with the aforementioned water-miscible organic solvents.

In a particularly preferred embodiment, the concentration of the acid in the aqueous solvent is selected such that the pH of the reaction mixture (comprising solvent and aniline III) is at most 7, for example from 0 to 7 or from 1 to 7 or from 2 to 7, preferably <7, for example from 0 to <7 or from 1 to <7 or from 2 to <7, more preferably at most 6, for example from 0 to 6 or from 1 to 6 or from 2 to 6, and even more preferably at most 5, for example from 0 to 5 or from 1 to 5 or from 2 to 5 or from 2 to 4; this applies to all embodiments of the process according to the invention [apart from the cases described below], but especially to the case that the decomposition of the diazonium salt of the formula II to nitrogen and aryl radical is brought about by the presence of at least reducing agent, in particular of at least one reducing metal salt and especially of at least one titanium(III) salt (see below). These pH values are employed irrespective of how the diazonium salt is decomposed, and preferably also when A' is $NR^5R^6$ and $R^5$ is H and $R^6$ is an (electron-withdrawing) protecting group and is preferably $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocarbonyl, di-($C_1$-$C_4$-alkyl)aminocarbonyl, $C_1$-$C_4$-alkylsulfonyl or $C_1$-$C_4$-haloalkylsulfonyl; or $R^5$ and $R^6$ together form an (electron-withdrawing) protecting group and preferably together form a =$CR^{12}$—$NR^{13}R^{14}$ group or, together with the nitrogen atom to which they are bonded, a $C_1$-$C_4$-alkylimino group or an aryl-$C_1$-$C_4$-alkylimino group (see also embodiments A-1, 2nd variant, and embodiment A-1.1).

In an alternatively particularly preferred embodiment, the pH of the reaction mixture (comprising solvent and aniline III) in the aqueous solvent is preferably 5 to 9, more preferably 5 to 8, even more preferably 5.5 to 7 and especially about 6; this applies to all embodiments of the process according to the invention (apart from the case described above), but especially to the case that the decomposition of the diazonium salt of the formula II to nitrogen and an aryl radical is brought about by performing step (i) in at least one solvent which brings about the free-radical decomposition of the diazonium salt for the formula II to nitrogen and an aryl radical and/or promotes the conversion to the compound I' in another way (see below), and also to the case that the decomposition of the diazonium salt of the formula II to nitrogen and an aryl radical is brought about by the presence of at least one reducing agent other than Ti(III) salts, and which comprises especially Cu(I) or Fe(II) salts (see below).

When A' in the aniline compounds III is $NR^5R^6$ in which $R^5$ and $R^6$ are each independently hydrogen, $C_1$-$C_{10}$-alkyl, $C_3$-$C_4$-alkenyl, $C_3$-$C_{10}$-cycloalkyl, aryl or aryl-$C_1$-$C_4$-alkyl, where the aryl groups of the 2 latter substituents optionally each bear 1, 2, 3 or 4 substituents which are selected from halogen, nitro, $C_1$-$C_4$-alkyl, $C_1$-$C_4$-haloalkyl, $C_1$-$C_4$-alkoxy and $C_1$-$C_4$-haloalkoxy, or is $(NR^7R^8R^9)^+V^-$, the concentration of the acid is preferably selected such that at most the acid monoaddition salt of III can be formed and the $NH_2$ group preferably remains unprotonated; this applies to all embodiments of the process according to the invention, but especially in the case that the decomposition of the diazonium salt of the formula II to nitrogen and an aryl radical is brought about by performing step (i) in at least one solvent which brings about the free-radical decomposition of the diazonium salt of the formula II to nitrogen and an aryl radical and/or promotes the conversion to the compound I' in another way (see below), and also to the case that the decomposition of the diazonium salt of the formula II to nitrogen and an aryl radical is brought about by the presence of at least one reducing agent other than Ti(III) salts, and which comprises especially Cu(I) or Fe(II) salts (see below). In other words, the concentration of the acid is preferably selected such that at least one amino group ($NH_2$ and/or $NR^5R^6$ where $R^5$ and $R^6$ are each as defined above, preferably $NH_2$) is present in free (i.e. unprotonated) form in the aniline compound III.

In the case that A' in the aniline compounds III is $NR^5R^6$ in which $R^5$ and $R^6$ are each independently hydrogen, $C_1$-$C_{10}$-alkyl, $C_3$-$C_4$-alkenyl, $C_3$-$C_{10}$-cycloalkyl, aryl or aryl-$C_1$-$C_4$-alkyl, where the aryl groups of the 2 latter substituents optionally each bear 1, 2, 3 or 4 substituents which are selected from halogen, nitro, $C_1$-$C_4$-alkyl, $C_1$-$C_4$-haloalkyl, $C_1$-$C_4$-alkoxy and $C_1$-$C_4$-haloalkoxy, or is $(NR^7R^8R^9)^+V^-$, in a particular embodiment, the concentration of the acid is preferably selected such that the amino group $NH_2$ is present in unprotonated form in the reaction mixture in at least 10 mol %, more preferably in at least 20 mol %, even more preferably in at least 50 mol % and especially in at least 70 mol % of the aniline compound III used. This applies to all embodiments of the process according to the invention (apart from the case of use of Ti(III) salts; see above and also remarks which follow), but especially in the case that the decomposition of the diazonium salt of the formula II to nitrogen and an aryl radical is brought about by performing step (i) in at least one solvent which brings about the free-radical decomposition of the diazonium salt of the formula II to nitrogen and an aryl radical and/or promotes the conversion to the compound I' in another way (see below), and also to the case that the decomposition of the diazonium salt of the formula II to nitrogen and an aryl radical is brought about by the presence of at least one reducing agent other than Ti(III) salts, and which comprises especially Cu(I) or Fe(II) salts (see below).

Also in the case that A' is halogen, $C_1$-$C_4$-alkyl, $C_1$-$C_4$-alkoxy, $C_1$-$C_4$-haloalkoxy, $C_1$-$C_4$-alkylcarbonyl, $C_1$-$C_4$-haloalkylcarbonyl, nitro, hydroxy, $SO_3R^3$, $COOR^2$, $CONR^{10}R^{11}$, $COR^4$, optionally substituted aryl or optionally substituted aryloxy, in a particular embodiment, the concentration of the acid is preferably selected such that the amino group $NH_2$ is present in unprotonated form in the reaction mixture in at least 10 mol %, more preferably in at least 20 mol %, even more preferably in at least 50 mol % and especially in at least 70 mol % of the aniline compound III used. This applies to all embodiments of the process according to the invention (apart from the case of use of Ti(III) salts; see above and also remarks which follow), but especially in the case that the decomposition of the diazonium salt of the formula II to nitrogen and an aryl radical is brought about by performing step (i) in at least one solvent which brings about the free-radical decomposition of the diazonium salt of the formula II to nitrogen and an aryl radical and/or promotes the conversion to the compound I' in another way (see below), and also to the case that the decomposition of the diazonium salt of the formula II to nitrogen and an aryl radical is brought about by the presence of at least one reducing agent other than Ti(III) salts, and which comprises especially Cu(I) or Fe(II) salts (see below).

Nonaqueous solvents are also suitable, for example the abovementioned water-miscible organic solvents and mixtures of these solvents.

When solvents with easily abstractable hydrogen atoms are used, such as primary alcohols (e.g. methanol, ethanol n-propanol or n-butanol), diols, ethers (especially the cyclic ethers, such as tetrahydrofuran and dioxane) or dimethylformamide, they are preferably used in the mixture with a solvent which has no easily abstractable hydrogen atoms, since they can give the best possible protection formed from undesired side reactions to an aryl radical. Examples of solvents which do not have any easily abstractable hydrogen atoms are water and aqueous mineral acids, such as hydrochloric acid, hydrobromic acid, nitric acid, sulfuric acid, phosphoric acid and the like, and also comparatively inert inorganic solvents such as acetonitrile, acetic acid, trifluoroacetic acid, acetone, trifluoroethanol, dimethyl sulfoxide or mixtures thereof, but also alcohols without hydrogen atoms in the a position, such as tert-butanol. Especially addition of water or aqueous mineral acids, such as hydrochloric acid, hydrobromic acid, nitric acid, sulfuric acid, phosphoric acid and the like, generally has a stabilizing effect on the aryl radicals which form since they enter into virtually no side reactions with water. Water and aqueous mineral acids are therefore preferred as solvents without abstractable hydrogen atoms. The solvents with easily abstractable hydrogen atoms, which are thus not inert with respect to the aryl radical and can therefore lead to undesired products, are present in an amount of at most 50% by weight, more preferably of at most 20% by weight and especially of at most 10% by weight, based on the weight of the mixture of solvents with and solvents without easily abstractable hydrogen atoms. Since the solvents without easily abstractable hydrogen atoms used are especially water or aqueous mineral acids, the solvents with easily abstractable hydrogen atoms used in the mixtures are preferably those which are miscible with water (these are the aforementioned alcohols, diols and cyclic ethers). It is alternatively possible to use, in the mixtures, solvents which have easily abstractable hydrogen atoms and which are immiscible or do not have good miscibility with water when a solubilizer is used at the same time. The term "solubilizer" refers to (interface-active) substances which, by virtue of their presence, make compounds which are virtually insoluble in a solvent soluble or emulsifiable in this solvent. The action is generally based on the fact that the solubilizers enter into a molecular bond or form micelles with the sparingly soluble substance. The first variant, however, is preferred.

A further suitable solvent system is a biphasic system which comprises two essentially mutually immiscible solvent systems. "Essentially immiscible" means that a first solvent which is used in a smaller amount than or an equal amount to a second solvent dissolves in the second solvent to an extent of at most 20% by weight, preferably to an extent of at most 10% by weight and especially to an extent of at most 5% by weight, based on the total weight of the first solvent. Examples are systems which, in addition to an above-defined aqueous solvent, comprise one or more essentially water-immiscible solvents, such as carboxylic esters, e.g. ethyl acetate, propyl acetate or ethyl propionate, open-chain ethers such as diethyl ether, dipropyl ether, dibutyl ether, methyl isobutyl ether and methyl tert-butyl ether, aliphatic hydrocarbons such as pentane, hexane, heptane and octane, and petroleum ether, halogenated aliphatic hydrocarbons such as methylene chloride, trichloromethane, dichloroethane and trichloroethane, cycloaliphatic hydrocarbons such as cyclopentane and cyclohexane, and aromatic hydrocarbons such as toluene, the xylenes, chlorobenzene, dichloro-benzenes and mesitylene. Such a biphasic solvent system may suitably also comprise at least one phase transfer catalyst. Suitable phase transfer catalysts are sufficiently well known to those skilled in the art and comprise, for example, charged systems such as organic ammonium salts, for example tetra($C_1$-$C_{18}$-alkyl)ammonium chlorides or bromides, such as tetramethylammonium chloride or bromide, tetrabutylammonium chloride or bromide, hexadecyltrimethylammonium chloride or bromide, octadecyltrimethylammonium chloride or bromide, methyltrihexylammonium chloride or bromide, methyltrioctylammonium chloride or bromide or benzyltrimethylammonium hydroxide (Triton B), and also tetra-($C_1$-$C_{18}$-alkyl) phosphonium chlorides or bromides such as tetraphenylphosphonium chloride or bromide, [(phenyl)$_m$-($C_1$-$C_{18}$-alkyl)$_n$]phosphonium chlorides or bromides in which m=from 1 to 3 and n=from 3 to 1 and the sum of m+n=4, and additionally pyridinium salts such as methylpyridinium chloride or bromide, and uncharged systems such as crown ethers or aza crown ethers, for example 12-crown-4, 15-crown-5,18-crown-6, dibenzo-18-crown-6 or [2,2,2]-cryptand (222-Kryptofix), cyclodextrins, calixarenes such as [14]-metacyclophane, calix[4]arene and p-tert-butyl-calix[4]arene, and cyclophanes.

In a preferred embodiment, the aqueous solvent is dilute mineral acid, i.e. a mineral acid is present in the aqueous solvent in a concentration of generally from 0.1 to 20% by weight, in particular from 3 to 15% by weight and especially from 2 to 8% by weight. The mineral acid used here is preferably hydrochloric acid.

The concentration of the acid in the aqueous solvent is preferably selected such that a pH of at most 7, for example from 0 to 7 or from 1 to 7 or from 2 to 7, and especially of at most 5, for example from 0 to 5 or from 1 to 5 or from 2 to 5 or from 3 to 4, is present in the reaction mixture.

In an alternatively preferred embodiment, the aqueous solvent comprises water or mixtures of water with water-miscible organic solvents (and without addition of acids or at most in such an amount that the pH of the reaction medium is at least 5); this applies to all embodiments of the process according to the invention (apart from the use of Ti(III) salts; see above and also remarks below), but especially in the case that the decomposition of the diazonium salt of the formula II to nitrogen and an aryl radical is brought about by performing step (i) in at least one solvent which brings about the free-radical decomposition of the diazonium salt of the formula II to nitrogen and an aryl radical and/or promotes the conversion to the compound I"—in another way (see below), and also in the case that the decomposition of the diazonium salt of the formula II to nitrogen and an aryl radical is brought about by the presence of at least one reducing agent other than Ti(III) salts, and which comprises especially Cu(I) or Fe(II) salts (see below); this additionally applies especially also in the case that A' is $NR^5R^6$ in which $R^5$ and $R^6$ are each independently hydrogen, $C_1$-$C_{10}$-alkyl, $C_3$-$C_4$-alkenyl, $C_3$-$C_{10}$-cycloalkyl, aryl or aryl-$C_1$-$C_4$-alkyl where the aryl group of the 2 latter substituents optionally each bear 1, 2, 3 or 4 substituents which are selected from halogen, nitro, $C_1$-$C_4$-haloalkyl, $C_1$-$C_4$-alkoxy and $C_1$-$C_4$-haloalkoxy, or is $(NR^7R^8R^9)^+V^-$.

In a preferred embodiment, the solvents are used in degassed form (i.e. especially in a form depleted in oxygen (i.e. in a form partially freed of oxygen) or even in a form substantially freed of oxygen). The solvents are preferably used in such a form that they comprise at most 70%, more preferably at most 50%, even more preferably at most 30% and especially at most 10% of the oxygen typically present in the particular solvent ("typically present" relates to the oxygen content as present in commercially available solvents or those obtained by customary processes, such as distillation). The degassing of solvents is known and can be effected, for example, by single or multiple freezing of the solvent, thawing under reduced pressure (to remove the gas dissolved/dispersed in the solvent) and compensating with an inert gas, such as nitrogen or argon. Alternatively or additionally, the solvent can be treated with ultrasound. The latter procedure is a possibility especially in the case of water or aqueous solvents, since the expansion of water in the course of freezing can lead to apparatus problems. It is assumed that the use of at least partially degassed solvent prevents a multiple arylation of the aniline compound III by II.

Preferably, in the process according to the invention for preparing aminobiphenyls of the formula (I), the diazonium salt of the formula (II) is used in an amount of from 0.001 to 0.9 mol, more preferably from 0.01 to 0.3 mol and especially from 0.02 to 0.1 mol, based in each case on 1 mol of the aniline derivative of the formula (III). It is assumed that the use of the diazonium salt II in deficiency prevents a multiple arylation of the aniline compound III by II.

Preference is given to using the aniline derivative (III) directly as the free amine. Alternatively, it can also be used, either completely or partially, in the form of one of its acid adducts or of a mixture of such adducts, particular preference being given to the hydrochloride of the compound (III). The acid adduct can also be formed in situ, specifically when the aniline compound (III) is initially charged in a dilute aqueous acid as the solvent. When A' in the aniline compounds III is $NR^5R^6$ in which $R^5$ and $R^6$ are each independently hydrogen, $C_1$-$C_{10}$-alkyl, $C_3$-$C_4$-alkenyl, $C_3$-$C_{10}$-cycloalkyl, aryl or aryl-$C_1$-$C_4$-alkyl, or is $(NR^7R^8R^9)^+V^-$, preferably at least one amino group ($NH_2$ and/or $NR^5R^6$, preferably $NH_2$) is present in free form in compound III, i.e. compound III is used in the form of no more than a monoacid adduct (e.g. monohydrochloride) (when A' is $(NR^7R^8R^9)^+V^-$, the amino group $NH_2$ in compound III is preferably not protonated). Irrespective of the definition of A', the aniline derivative (III) is more preferably used directly as a free amine.

As already stated, in a preferred embodiment, the diazonium salt (II) is added to the aniline compound (III) present in the initial charge. The diazonium salt can be added either in substance or dissolved or dispersed in a solvent. The solvents used here may be the abovementioned aqueous solvents or polar organic solvents, preference being given to the aforementioned water-miscible organic solvents. The diazonium salt (II) is preferably added gradually (in portions or continuously). In many cases, gradual addition suppresses the formation of homo-coupling products, i.e. of products which arise through reaction of two or more diazonium molecules (II) with one another, since a low concentration of the diazonium salt (II) in the reaction mixture ensures that its reaction with the aniline (III) predominates over the reaction with itself. The rate of addition is determined by several factors, such as batch size, temperature, reactivity of the reactants and type of the reaction conditions selected, which bring about decomposition of the diazonium salt of the formula II to nitrogen and an aryl radical, and can be determined by the person skilled in the art in the individual case, for example by suitable preliminary tests. For instance, a low reactivity of the reactants requires a relatively slow rate of addition, but this can be compensated for at least partly, for example, by a higher temperature and/or by the selection of reaction conditions which accelerate decomposition of the diazonium salt.

It is suspected that the two aforementioned preferred measures, the use of the diazonium compound (II) in deficiency and the stepwise addition thereof, generally bring about an advantageous reaction, since they suppress the homo-coupling of the compound (II).

The reaction temperature of step (i) is determined by several factors, for example the reactivity of the reactants used and the type of reaction conditions selected, which bring about decomposition of the diazonium salt of the formula II to nitrogen and an aryl radical, and can be determined in the individual case by the person skilled in the art, for example by simple preliminary tests. In general, the reaction in step (i) of the compound of the formula (II) with the compound of the formula (III) is carried out at a temperature in the range from preferably −10° C. up to the boiling point of the reaction mixture, preferably from −10 to 100° C., more preferably from 0 to 80° C. and especially from 0 to 30° C. These temperatures apply to performance of step (i) in solution; when it is, in contrast, carried out in bulk and the melting point of the aniline III is above room temperature, the reaction temperature of course corresponds at least to the temperature of the melt of the reaction mixture.

The intended result of the above-described conditions, especially pH values, is that the process according to the invention leads preferentially to 2-aminobiphenyls, and the formation of the competing positional isomer (3-aminobiphenyls) is suppressed. A preferred embodiment (embodiment A-1) of process A therefore relates to a process for preparing 2-aminobiphenyls of the formula (IA),

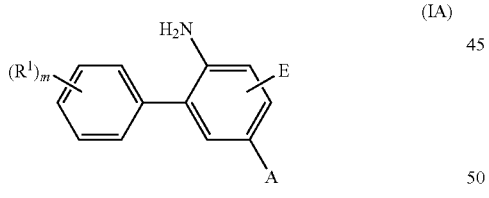

(IA)

in which $R^1$, m, A and E are each as defined above, comprising the following steps:

(i) reacting a diazonium salt of the formula (II) with an aniline derivative of the formula (III)

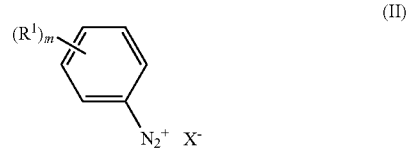

(II)

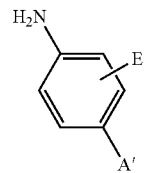

(III)

in which
A' is as defined for A, with the proviso that A' is not hydrogen;
$X^-$ is a monovalent anion or the portion of a polyvalent anion equivalent to a monovalent anion, and
m, E and $R^1$ are each as defined above,
under reaction conditions which can bring about decomposition of the diazonium salt of the formula II to nitrogen and an aryl radical
to obtain an aminobiphenyl of the formula (I'),

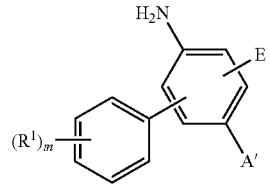

(I')

(i-a) if required, removing isomer I'B from isomer I'A

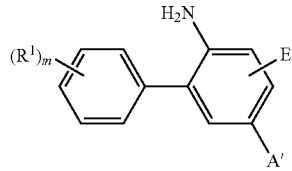

(I'A)

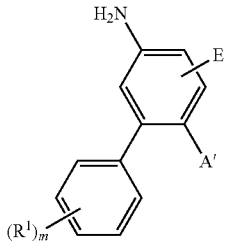

(I'B)

and
(ii) optionally converting the aminobiphenyl of the formula (I'A) obtained in step (i) or (i-a) to an aminobiphenyl of the formula (IA) in which A is hydrogen; or
(i-b1) in the case that A' is $NR^5R^6$ in which
$R^5$ is H; and
$R^6$ is a protecting group and is preferably $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocarbonyl, di-($C_1$-$C_4$-alkyl)-aminocarbonyl, $C_1$-$C_4$-alkylsulfonyl or $C_1$-$C_4$-haloalkylsulfonyl; or
$R^5$ and $R^6$ together form a protecting group and preferably together form a $=CR^{12}$—$NR^{13}R^{14}$ group or, together with the nitrogen atom to which they are bonded, a $C_1$-$C_4$-alkylimino group or an aryl-$C_1$-$C_4$-alkylimino group:
if required, removing isomer I'A from isomer I'B;
(i-b2) removing the amino group of the aminobiphenyl (I'B) obtained in step (i) or (i-b1) to obtain a biphenyl of the formula (XII)

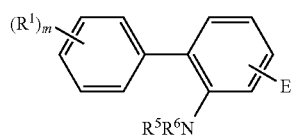

and
(i-b3) removing the $R^6$ and if required $R^5$ radical to obtain a compound (IA) in which A is H.

It will be appreciated that any required and desired isomer separations [steps (i-a) and (i-b1)] may also be carried out at another time. For example, in the first variant, the substituent A' in the compound I'A can first be converted to hydrogen [step (ii)] and the isomer mixture separated only thereafter, and equally, in the 2nd variant, step (i-b2) may directly follow step (i) and the isomer separation, if required and/or desired, can be effected only after step (i-b2) or even only after step (i-b3).

Isomers I'A and I'B may be isomer mixtures when E is not H. For instance, the aryl group may be bonded either on the same side as or on the opposite side from E (with regard to an axis formed by the $NH_2$ group and A'); preferably, however, for steric reasons, it is bonded on the opposite side, such that I'A and I'B are essentially not isomer mixtures.

It is obvious that the compound (IA) obtained in step (i-b3) comprises the E group bonded at a different position in relation to the amino group $NH_2$ than the compound (IA) which is obtained via the first variant [step (i-a) and optionally (ii)], since the amino group in the 2nd variant [steps (i-b1), (i-b2), (i-b3)] originates from the original A' group.

The desired isomers [(I'A in the first variant or (I'B) in the second variant) are obtained in sufficient excess (over the undesired isomer) or even selectively especially when the above-described pH ranges are maintained. For instance, isomer I'A is obtained preferentially (i.e. in excess over the undesired isomer I'B) or even selectively when A' has one of the general definitions given above and is preferably $NR^5R^6$, $(NR^7R^8R^9)^+V^-$, halogen, $C_1$-$C_4$-alkyl, $C_1$-$C_4$-haloalkyl, $C_1$-$C_4$-alkylcarbonyl, $C_1$-$C_4$-haloalkylcarbonyl, nitro, $SO_3R^3$, $COOR^2$, $CONR^{10}R^{11}$, $COR^4$ or optionally substituted aryl, and step (i) is performed at a pH of 5 to 9, preferably 5 to 8, particularly 5.5 to 7 and especially about 6. Isomer I'B is obtained, in contrast, preferentially or even selectively when A' is $NR^5R^6$ and $R^5$ is H and $R^6$ is an (electron-withdrawing) protecting group and is preferably $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocarbonyl, di-($C_1$-$C_4$-alkyl)aminocarbonyl, $C_1$-$C_4$-alkylsulfonyl or $C_1$-$C_4$-haloalkylsulfonyl; or $R^5$ and $R^6$ together form an (electron-withdrawing) protecting group and preferably both together form a $=CR^{12}$—$NR^{13}R^{14}$ group or a $=C$—$N(CH_3)_2$ group, or together with the nitrogen atom to which they are bonded form a $C_1$-$C_4$-alkylimino group or an aryl-$C_1$-$C_4$-alkylimino group, and step (i) is performed at a pH of at most 7, for example from 0 to 7 or from 1 to 7 or from 2 to 7, preferably <7, for example from 0 to <7 or from 1 to <7 or from 2 to <7, more preferably at most 6, for example from 0 to 6 or from 1 to 6 or from 2 to 6, and especially at most 5, for example from 0 to 5 or from 1 to 5 or from 2 to 5 or from 2 to 4.

Preference is given to selecting the first variant of embodiment A-1 when A' is $(NR^7R^8R^9)^+V^-$, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl, $C_1$-$C_4$-haloalkylcarbonyl, nitro, hydroxyl, $SO_3R^3$, $COOR^2$, $CONR^{10}R^{11}$, $COR^4$, optionally substituted aryl, optionally substituted aryloxy or $NR^5R^6$ in which $R^5$ and $R^6$ each have one of the definitions given above and are preferably each independently hydrogen, $C_1$-$C_{10}$-alkyl, $C_3$-$C_4$-alkenyl, $C_3$-$C_{10}$-cycloalkyl, optionally substituted aryl or optionally substituted aryl-$C_1$-$C_4$-alkyl, and especially when A' is $NH_2$, and to performing step (i) in this case at a pH in the range from preferably 5 to 9, more preferably from 5 to 7, especially from 5.5 to 7 and particularly about 6. This variant is also preferred when A' is $NR^5R^6$ in which $R^5$ is hydrogen and $R^6$ is an (electron-withdrawing) protecting group and is preferably $C_1$-$C_4$-alkylcarbonyl, $C_1$-$C_4$-haloalkyl-carbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocarbonyl, di-($C_1$-$C_4$-alkyl)aminocarbonyl, $C_1$-$C_4$-alkylsulfonyl or $C_1$-$C_4$-haloalkylsulfonyl; or $R^5$ and $R^6$ together form an (electron-withdrawing) protecting group and preferably both together form a $=CR^{12}$—$NR^{13}R^{14}$ group, or together with the nitrogen atom to which they are bonded form a $C_1$-$C_4$-alkylimino group or an aryl-$C_1$-$C_4$-alkylimino group (see below), and a product which is to contain two amino groups ($NH_2$ and $NR^5R^6$) is to be obtained (in contrast to the second variant, in which the $NH_2$ group is of course removed).

The second variant of embodiment A-1 is preferably selected when A' is $NR^5R^6$ in which $R^5$ is hydrogen and $R^6$ is an (electron-withdrawing) protecting group and is preferably $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkyl-aminocarbonyl, di-($C_1$-$C_4$-alkyl)aminocarbonyl, $C_1$-$C_4$-alkylsulfonyl or $C_1$-$C_4$-haloalkylsulfonyl; or $R^5$ and $R^6$ together form an (electron-withdrawing) protecting group and preferably both together form a $=CR^{12}$—$NR^{13}R^{14}$ group, or together with the nitrogen atom to which they are bonded form a $C_1$-$C_4$-alkyliminogroup or an aryl-$C_1$-$C_4$-alkylimino group, and step (i) is performed at a pH of at most 7, for example from 0 to 7 or from 1 to 7 or from 2 to 7, preferably <7, for example from 0 to <7 or from 1 to <7 or from 2 to <7, more preferably at most 6, for example from 0 to 6 or from 1 to 6 or from 2 to 6, and especially at most 5, for example from 0 to 5 or from 1 to 5 or from 2 to 5 or from 2 to 4.

A particular embodiment of the second variant (embodiment A-1.1) relates to a process for preparing 2-aminobiphenyls of the general formula (X),

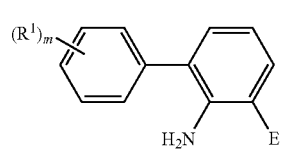

in which
R¹, E and m are each as defined in claim 1,
comprising the following steps:
(i) reacting a diazonium salt of the general formula (II) with an aniline derivative of the general formula (III'),

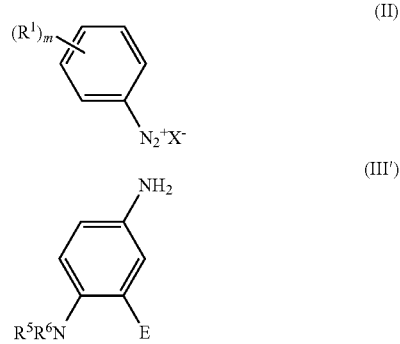

in which X⁻, R¹, E and m are each as defined in claim 1; R⁵ is H; and
R⁶ is a protecting group and is preferably $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocarbonyl, di-($C_1$-$C_4$-alkyl)-aminocarbonyl, $C_1$-$C_4$-alkylsulfonyl or $C_1$-$C_4$-haloalkylsulfonyl; or
R⁵ and R⁶ together form a protecting group and preferably together form a =CR¹²—NR¹³R¹⁴ group or a =C—N(CH₃)₂ group or, together with the nitrogen atom to which they are bonded, a $C_1$-$C_4$-alkylimino group or an aryl-$C_1$-$C_4$-alkylimino group;
under reaction conditions which can bring about decomposition of the diazonium salt of the formula (II) to nitrogen and an aryl radical
to obtain an aminobiphenyl of the formula (XI)

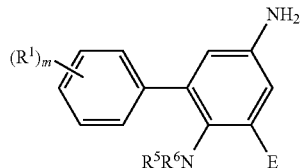

(i-b2) removing the amino group of the aminobiphenyl obtained in step (i) to obtain a biphenyl of the formula (XII)

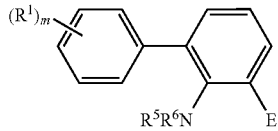

and
(i-b3) removing the R⁶ and if required R⁵ radical to obtain the compound (X).

In this embodiment A-1.1 and in the 2nd variant of embodiment A-1, the protecting groups R⁶ or the combined protecting groups R⁵ and R⁶ are selected such that they are essentially stable under the given reaction conditions and are not removed. In order, on the other hand, to ensure a high regioselectivity of the attack of the aryl radical which forms from the diazonium salt (II), the protecting groups are suitably selected such that the NR⁵R⁶ group is ortho-directing overall. "Essentially stable" means that the protecting groups R⁶ and, if present as a protecting group, R⁵ are removed in the course of step (i) in at most 10 mol %, preferably in at most 5 mol % and especially in at most 2 mol % of the aniline compounds (III) used.

When the reaction in step (i) is effected under acidic conditions, the protecting groups are preferably selected such that they are firstly hydrolysis-stable under acidic conditions, especially at a pH of from 0 to 7, preferably from 0.5 to 7, more preferably from 1 to 7 and especially from 2 to 7, and secondly lower the Lewis basicity of the nitrogen atom to which they are bonded to such an extent that it is essentially unprotonated in the pH value range specified. "Essentially unprotonated" means that the nitrogen atom which bears the R⁵ and R⁶ radicals is protonated in at most 10 mol %, preferably in at most 5 mol % and especially in at most 2 mol % of the aniline compounds (III) or (III') used. "Essentially hydrolysis-stable" means that the R⁶ radical and, if present as a protecting group, R⁵ are hydrolyzed in the course of step (i) in at most 10 mol %, preferably in at most 5 mol % and especially in at most 2 mol % of the aniline compounds (III) or (III') used.

According to the invention, the compounds (II) and (III) or (III') are converted in step (i) under reaction conditions which bring about decomposition of the diazonium salt of the formula II to nitrogen and an aryl radical. Preference is given to selecting reaction conditions under which a single electron is transferred to the diazonium salt (SET; single electron transfer).

Suitable conditions under which a decomposition of the diazonium salt of the formula II to nitrogen and an aryl radical takes place are common knowledge to those skilled in the art. For instance, even the addition of the diazonium salt (II) to the aniline derivative (III) or (III') can bring about the decomposition thereof to nitrogen and an aryl radical, since at least some of the aniline compounds (III) (for example phenylenediamine and other anilines III with equally strong or stronger reducing action) possess sufficient reductive potential. In this case, no specific process measures have to be taken and the reaction can be carried out under the above-described reaction conditions. When the reduction potential of the aniline (III) is insufficient, it is necessary to take further process measures in order to initiate the reduction step. However, even if the reduction potential of the aniline used should be sufficient to initiate the decomposition of the diazonium salt of the formula II to nitrogen and an aryl radical, it may be advantageous to take further process measures which ensure/accelerate decomposition or degradation of the diazonium salt of the formula II to nitrogen and an aryl radical or cause it to proceed preferentially over other possible reactions of the diazonium salt (e.g. azo coupling).

Preference is given to those process measures selected from the following:
a) performance of step (i) in the presence of at least one reducing agent;
b) performance of step (i) while irradiating with electromagnetic radiation in the visible and/or ultraviolet range;
c) performance of step (i) employing ultrasound;
d) performance of step (i) under the conditions of an electrochemical reduction;
e) performance of step (i) in at least one solvent which brings about the free-radical decomposition of the diazonium salt of the formula II to nitrogen and an aryl radical and/or promotes the conversion to the compound I' in another way;

f) performance of step (i) under radiolysis conditions; and
g) a combination of at least two of these measures.

a) Performance of Step (i) in the Presence of at Least One Reducing Agent

The term "reducing agent" refers to those elements and compounds which, as electron donors (including electron donor complexes), aim to be converted to a lower-energy state by the release of electrons, in particular to form stable electron shells. One measure of the strength of a reducing agent is the redox potential.

When step (i) is performed in the presence of a reducing agent, it is performed preferably in such a way that the aniline compound (III) or (III') and the reducing agent, preferably dissolved/dispersed in a solvent, are initially charged and admixed gradually with the diazonium salt (II). With regard to rate of addition, reaction temperature and solvent, reference is made to the above remarks.

The at least one reducing agent is preferably selected from reducing metal salts, reducing metals and reducing anions; however, other reducing agents whose reduction potential is sufficiently great to transfer an electron to the diazonium salt II used in each case are also suitable. These include different compounds, such as pyrene, ascorbic acid and hemoglobin. However, preference is given to the use of reducing metal salts and reducing anions.

Generally, it is possible to use any reducing metal salts for the inventive reaction of the compounds (II) and (III) or (III'), provided that their reduction potential is sufficiently great to transfer an electron to the diazonium salt II used in each case. In the context of the present invention, reducing metal salts are understood to mean those in which, under the reaction conditions of step (i), the most stable oxidation number of the metal is higher than in the form used, and so the metal acts as a reducing agent.

Preferred metal salts are soluble in the reaction medium. Since the reaction medium is preferably aqueous, preferred reducing metal salts are accordingly water-soluble. Preferred counterions of the metal salts are typical water-soluble anions, such as the halides, especially chloride, sulfate, nitrate, acetate and the like. However, metal complexes are also suitable, such as hexacyanoferrate(II) or ferrocene.

Particularly preferred reducing metal salts are selected from Ti(III) salts, Cu(I) salts, Fe(II) salts, tin(II) salts, chromium(II) salts and vanadium(II) salts, and especially from Ti(III) salts, Cu(I) salts and Fe(II) salts. Among these, preference is given to the water-soluble salts thereof, such as the chlorides, sulfates, nitrates, acetates and the like. In particular, Ti(III) salts are used, and especially $TiCl_3$.

Preference is given to using the reducing metal salt(s) in a total amount of from 0.005 to 8 mol, more preferably from 0.1 to 6 mol, even more preferably from 0.5 to 6 mol, even more preferably from 1 to 6 mol and especially from 2 to 5 mol, based on 1 mol of the diazonium salt (II).

When reaction step (i) is performed in degassed solvents (i.e. at least partially freed of oxygen; see above) and under an inert gas atmosphere, such as nitrogen or argon, the reducing metal salt can be used in smaller amounts, for example in an amount of from 0.005 to 4 mol, preferably from 0.01 to 1 mol, more preferably from 0.05 to 0.7 mol, even more preferably from 0.05 to 0.5 mol and especially from 0.05 to 0.4 mol, based on 1 mol of the diazonium salt (II).

Preferred reducing metals are selected from iron, copper, cobalt, nickel, zinc, magnesium, titanium and chromium, and more preferably from iron and copper.

The reducing metal(s) are preferably used in a total amount of 0.005 to 8 mol, more preferably of 0.1 to 6 mol, even more preferably of 0.5 to 3 mol, still more preferably of 0.1 to 1 mol and especially of 0.25 to 1 mol, based on 1 mol of the diazonium salt (II).

Suitable reducing anions are, for example, bromide, iodide, sulfite, hydrogensulfite, pyrosulfite, dithionite, thiosulfate, nitrite, phosphite, hypophosphite, $ArS^-$, xanthates ($ROCS_2^-$; $R=C_1-C_4$-alkyl, aryl), $C_1-C_4$-alkoxides such as methoxide, ethoxide, propoxide, isopropoxide, butoxide, isobutoxide and tert-butoxide, and phenoxide. When step (i) is performed under acidic conditions, the reducing anions are of course preferably selected from those whose reduction potential is still sufficient even under these conditions to bring about the decomposition of the diazonium salt.

The reducing anions are used in an amount of preferably from 0.005 to 8 mol, more preferably from 0.01 to 6 mol and especially from 1 to 6 mol, based on 1 mol of the diazonium salt (II).

However, preference is given to using, in step (i), the abovementioned reducing metal salts as reducing agents. With regard to suitable and preferred metal salts, reference is made to the above remarks.

b) Performance of Step (i) while Irradiating with Electromagnetic Radiation in the Visible and/or Ultraviolet Range Alternatively or additionally, in a preferred embodiment of the process according to the invention, step (i) is performed while irradiating with electromagnetic radiation in the visible and/or ultraviolet range. Preference is given to using electromagnetic radiation with a wavelength in the range from 100 to 400 nm, more preferably in the range from 200 to 380 nm and especially in the range from 250 to 360 nm.

Step (i) with irradiation is performed preferably in such a way that the aniline compound (III) or (III') is initially charged in a suitable solvent and is irradiated while cooling during the gradual addition of the diazonium salt (II). Especially when UV radiation is used, the solvents are preferably used in degassed form, since oxygen radicals can otherwise form and may lead to undesired products. Since water or aqueous solutions cannot be degassed in a trivial manner, the abovementioned organic solvents are possibilities in this case.

c) Performance of Step (i) Employing Ultrasound

Alternatively or additionally, in a preferred embodiment of the process according to the invention, step (i) is performed employing ultrasound. Like all soundwaves, ultrasound also causes periodic compression and expansion of the medium; the molecules are forced together and stretched. They form small bubbles which grow and immediately implode again. This phenomenon is known as cavitation. Each imploding bubble emits shockwaves and tiny liquid jets with a speed of about 400 km/h, which act on the immediate environment. Cavitation can be exploited, for example, in order to accelerate chemical reactions and to increase the solubility of products in a particular medium.

Step (i) employing ultrasound can be performed, for example, in such a way that the reaction vessel in which the aniline compound (III) or (III') is initially charged in a suitable solvent is present in an ultrasound bath, and the reaction mixture is exposed to ultrasound during the gradual addition of the diazonium salt (II). Instead of the use of an ultrasound bath, a sonotrode (=device which transmits the ultrasound vibrations generated by a sound transducer to the material to be subjected to ultrasound) may be mounted in the reaction vessel in which the aniline compound (III) or (III') is initially charged in a suitable solvent. The latter alternative is possible especially for relatively large batches.

With regard to rate of addition, reaction temperature and solvent, reference is made to the above remarks.

d) Performance of Step (i) Under the Conditions of an Electrochemical Reduction

Alternatively or additionally, in a preferred embodiment of the process according to the invention, step (i) is performed under the conditions of an electrochemical reduction. In this procedure, in a formal sense, nitrogen radicals from the diazonium salt (II) are reduced cathodically, which accelerates the decomposition of the diazonium salt to aryl radical and nitrogen.

The performance is effected, for example, in such a way that cathode and anode are arranged in the reaction vessel which comprises the aniline compound (III) or (III') initially charged in a suitable solvent, and voltage is applied during the gradual addition of the diazonium salt (II). The voltage and current density to be selected depends on various factors, such as rate of addition and solvent, and has to be determined in the individual case, which is done, for example, with the aid of preliminary tests. The solvents are suitably selected such that they as far as possible do not enter into any competing reaction at the electrodes under the given reaction conditions. Since the cathodic reduction of protons can be avoided only with difficulty even in the case of very low current densities and voltage, preference is given to using aprotic, polar solvents, such as acetonitrile, dimethylformamide or acetone.

e) Performance of step (i) in at least one solvent or solvent system which brings about the free-radical decomposition of the diazonium salt of the formula (II) to nitrogen and an aryl radical and/or promotes the conversion to the compound (I) in another way Alternatively or additionally, in a preferred embodiment of the process according to the invention, step (i) is performed in at least one solvent which brings about the free-radical decomposition of the diazonium salt of the formula II to nitrogen and an aryl radical, and/or promotes the conversion to the compound I' in another way. "In another way" means, for example, that the solvent stabilizes the aryl radical formed in the decomposition, which prevents or at least reduces undesired side reactions.

Solvents which promote the free-radical decomposition of the diazonium salt II to an aryl radical feature a certain reductive potential and can act in conjunction with a diazonium salt as a reducing agent; in other words, the solvents themselves are oxidizable. Examples of such solvents are alcohols, e.g. $C_1$-$C_4$-alcohols, such as methanol, ethanol, propanol, isopropanol, butanol, sec-butanol, isobutanol and tert-butanol, diols such as ethylene glycol and diethylene glycol, open-chain ethers such as diethyl ether, methyl isobutyl ether and methyl tert-butyl ether, cyclic ethers such as tetrahydrofuran and dioxane, nitrogen-containing heterocycles such as pyridine, and HMP (hexamethylphosphoramide), but also basic aqueous solutions. Since, however, basic solutions promote or at least do not suppress side reactions, such as the azo coupling of the diazonium salt, the pH of the reaction mixture should not exceed a value of 9. Suitable bases are inorganic bases, such as alkali metal hydroxides, e.g. lithium, sodium or potassium hydroxide, alkaline earth metal hydroxides, e.g. magnesium or calcium hydroxide, alkali metal carbonates, e.g. lithium, sodium or potassium carbonate, and alkali metal hydrogencarbonates, e.g. lithium, sodium or potassium hydrogencarbonate, and organic bases such as acetates, e.g. sodium acetate, or alkoxides, e.g. sodium methoxide, sodium ethoxide, sodium tert-butoxide or potassium tert-butoxide. Among the aforementioned reducing solvents, preference is given especially to those which possess no easily abstractable hydrogen atoms, for example alcohols without hydrogen atoms in the α-position, such as tert-butanol, since they essentially do not enter into any undesired side reactions with the aryl radical formed.

However, suitable solvents are also those which do not have reductive action under the given reaction conditions but do not possess any easily abstractable hydrogen atoms since they can provide the best possible protection for an aryl radical formed from undesired side reactions. At the same time, however, the solvents must also have sufficient dissolution capacity for the reactants. Examples thereof are water and aqueous mineral acids, such as hydrochloric acid, hydrobromic acid, nitric acid, sulfuric acid, phosphoric acid and the like, or comparatively inert organic solvents, such as acetonitrile, acetic acid, trifluoroacetic acid, acetone, trifluoroethanol, dimethyl sulfoxide or mixtures thereof, but also alcohols with no hydrogen atoms in the α-position, such as tert-butanol. Especially an addition of water or aqueous mineral acids, such as hydrochloric acid, hydrobromic acid, nitric acid, sulfuric acid, phosphoric acid and the like, generally has a stabilizing effect on the aryl radicals which form, since they enter into virtually no side reactions with water. Water and aqueous mineral acids are therefore preferred as solvents without abstractable hydrogen atoms. On the other hand, excessive protonation of the aniline compound III (especially when A' is $NR^5R^6$ or $(NR^7R^8R^9)^+V^-$) can lead to a multiple arylation by II, which leads to undesired by-products. Therefore, in the case that A' is $NR^5R^6$ or $(NR^7R^8R^9)^+V^-$, it is preferred to select the pH of the reaction mixture such that at least one amino group ($NH_2$ and/or $NR^5R^6$) in the aniline compound A' is present in free form (i.e. in unprotonated form; as $NH_2$ or $NR^5R^6$). Irrespective of the definition of A', it is preferred that the pH is selected such that the amino group $NH_2$ in the reaction mixture is present in unprotonated form in at least 10 mol %, more preferably in at least 20 mol %, even more preferably in at least 50 mol % and especially in at least 70 mol % of the aniline compound III used; however, this is not the case for the 2nd variant of embodiment A-1 and of embodiment A-1.1.

The pH of the reaction mixture is preferably 5 to 9, more preferably 5 to 8, even more preferably 5.5 to 7 and especially about 6. In particular, water is used (without addition of acid or in such an amount that the pH is at least 5) as the solvent. To establish the pH above 7, customary water-soluble inorganic bases are generally used, such as alkali metal hydroxides, e.g. sodium or potassium hydroxide, alkali metal carbonates, such as sodium or potassium carbonate, or alkali metal hydrogencarbonates, such as sodium or potassium hydrogencarbonate, or water-soluble organic bases such as diethylamine or triethylamine.

When solvents with easily abstractable hydrogen atoms, such as primary alcohols, are used, they are preferably used in a mixture with a solvent which possesses no easily abstractable hydrogen atoms. Preferably, the solvents with easily abstractable hydrogen atoms, which as a result are not inert to the aryl radical and can therefore lead to undesired products, are present in an amount of at most 50% by weight, more preferably of at most 20% by weight and especially of at most 10% by weight, based on the weight of the mixture composed of solvents with and solvents without easily abstractable hydrogen atoms. Since the solvents without easily abstractable hydrogen atoms used are especially water or dilute aqueous mineral acids, the solvents with easily abstractable hydrogen atoms used in the mixtures are preferably those which are miscible with water (these are the aforementioned alcohols, diols and cyclic ethers). Alternatively, it is possible in the mixtures to use solvents which have easily abstractable hydrogen atoms and which are immiscible or do not have good miscibility with water when a solubilizer is used at the same time. The term "solubilizer" refers to (interface-active) substances which, by virtue of their presence, make other compounds which are virtually insoluble in a solvent soluble or emulsifiable in this solvent. The action is generally based on the fact that the solubilizers enter into a molecular bond or form micelles with the sparingly soluble substance. The first variant, however, is preferred.

Overall, the solvents used which bring about the free-radical decomposition of the diazonium salt of the formula II to nitrogen and an aryl radical and/or promote the conversion to the compound I' in another way are preferably water, the dilute aqueous mineral acids mentioned or mixtures of the abovementioned organic, water-miscible solvents having a certain reduction potential (these are the aforementioned alcohols, diols and cyclic ethers) with water or the dilute aqueous acids mentioned. Particular preference is given to using water or mixtures of the abovementioned organic, water-miscible solvents having a certain reduction potential (these are the aforementioned alcohols, diols and cyclic ethers) with water.

In a preferred embodiment, the solvents are used in degassed form (i.e. especially at least partially freed of oxygen; see above). With regard to the degassing, reference is made to the above remarks.

Also suitable is performance in a biphasic system, in which case one of the phases comprises at least one of the abovementioned solvents and the second phase is essentially immiscible with the first phase. The first phase preferably comprises at least one of the abovementioned protic solvents, such as water, alcohols or diols. The first phase is more preferably an aqueous system, i.e. the solvent used is water, an aqueous mineral acid such as hydrochloric acid, hydrobromic acid, nitric acid, sulfuric acid, phosphoric acid and the like, or a mixture of water and of an aqueous acid with at least one water-miscible organic solvent, e.g. $C_1$-$C_4$-alcohols such as methanol, ethanol, propanol, isopropanol or trifluoroethanol, diols such as ethylene glycol, cyclic ethers such as tetrahydrofuran and dioxane, acetonitrile, amides such as dimethylformamide, carboxylic acids such as glacial acetic acid/ acetic acid, and ketones such as acetone. In particular, the first phase comprises water or an aqueous mineral acid, in which case the mineral acid is preferably hydrochloric acid or hydrobromic acid.

The second phase is preferably selected from carboxylic esters, for example ethyl acetate, propyl acetate or ethyl propionate, open-chain ethers such as diethyl ether, dipropyl ether, dibutyl ether, methyl isobutyl ether and methyl tert-butyl ether, aliphatic hydrocarbons such as pentane, hexane, heptane and octane, and petroleum ether, halogenated aliphatic hydrocarbons such as methylene chloride, trichloromethane, tetrachloromethane, dichloroethane and trichloroethane, cycloaliphatic hydrocarbons such as cyclopentane and cyclohexane, and aromatic hydrocarbons such as toluene, the xylenes, chlorobenzene or dichlorobenzene.

Such a biphasic solvent system may also comprise at least one phase transfer catalyst. Suitable phase transfer catalysts are sufficiently well known to those skilled in the art and comprise, for example, charged systems such as organic ammonium salts, for example tetra($C_1$-$C_{18}$-alkyl)ammonium chlorides or bromides, such as tetramethylammonium chloride or bromide, tetrabutylammonium chloride or bromide, hexadecyltrimethylammonium chloride or bromide, octadecyltrimethylammonium chloride or bromide, methyltrihexylammonium chloride or bromide, methyltrioctylammonium chloride or bromide or benzyltrimethylammonium hydroxide (Triton B), and also tetra-($C_1$-$C_{18}$-alkyl)phosphonium chlorides or bromides such as tetraphenylphosphonium chloride or bromide, [(phenyl)$_m$-($C_1$-$C_{18}$-alkyl)$_n$]phosphonium chlorides or bromides in which m=from 1 to 3 and n=from 3 to 1 and the sum of m+n=4, and additionally pyridinium salts such as methylpyridinium chloride or bromide, and uncharged systems such as crown ethers or aza crown ethers, for example 12-crown-4,15-crown-5,18-crown-6, dibenzo-18-crown-6 or [2,2,2]-cryptand (222-Kryptofix), cyclodextrins, calixarenes such as [14]-metacyclophane, calix[4]arene and p-tert-butyl-calix[4]arene, and cyclophanes.

In a preferred embodiment, the solvents are used in degassed form (i.e. especially at least partially freed of oxygen). With regard to the degassing, reference is made to the above remarks.

Overall, the solvents used which bring about the free-radical decomposition of the diazonium salt of the formula (II) to nitrogen and an aryl radical and/or promote the conversion to the compound (I) in another way, are more preferably water, the aqueous mineral acids mentioned or mixtures of the abovementioned organic, water-miscible solvents having a certain reduction potential (these are the aforementioned alcohols, diols and cyclic ethers) with water or the aqueous acids mentioned. The solvent used in step (i) is especially water or an aqueous mineral acid, for example dilute hydrochloric acid, which brings about the free-radical decomposition of the diazonium salt of the formula (II) to nitrogen and an aryl radical and/or promotes the reaction to give the compound (I) in another way. In a preferred embodiment, this is used in degassed form (i.e. especially freed of oxygen). With regard to the degassing, reference is made to the above remarks.

The performance is effected, for example, in such a way that the aniline compound (III) is initially charged in such a solvent (system) and then the diazonium salt is added gradually or, conversely, the diazonium salt (II) is initially charged in such a solvent (system) and then the aniline compound (III) or (III') is added, preference being given to the first variant. With regard to the rate of addition and reaction temperature, reference is made to the above remarks. In the case of performance in a biphasic system, it is alternatively possible to in each case initially charge the aniline compound (III) in the solvent (mixture) of the first phase and the diazonium salt in the solvent (mixture) of the second phase.

f) Performance of Step (i) Under Radiolysis Conditions

Alternatively or additionally, in a preferred embodiment of the process according to the invention, step (i) is performed under radiolysis conditions. In this case, solvated electrons are generated in aqueous solution by irradiating with γ-radiation, for example from a $^{60}$Co source. This procedure is described in detail in J. E. Packer et al., J. Chem. Soc., Perkin Trans. 2, 1975, 751 and in Aust. J. Chem. 1980, 33, 965, which are hereby fully incorporated by reference.

Among the measures mentioned, preference is given to performing step (i) in the presence of at least one reducing agent and especially of at least one reducing metal salt [measure a)].

Alternatively preferable is the performance of step (i) in the (sole) presence of at least one solvent which brings about the free-radical decomposition of the diazonium salt of the formula II to nitrogen and an aryl radical, and/or promotes the conversion to the compound I' in another way, especially of water, of one of the abovementioned dilute aqueous mineral acids or of a mixture of the reductive, organic, water-miscible solvents mentioned with water or one of the abovementioned dilute aqueous mineral acids, and especially of water or of a mixture of the reductive organic water-miscible solvents mentioned with water [measure e)]. Preference is given to using the solvents in degassed form. This embodiment is suitable especially when an aniline with a relatively high reduction potential, such as phenylenediamine, is used, which acts as a reducing agent for the diazonium salt.

When two or more of the above measures are combined, one of these measures is preferably the performance of step (i) in the presence of at least one reducing agent and especially of at least one reducing metal salt and/or the performance of step (i) in the presence of at least one solvent which brings about the free-radical decomposition of the diazonium salt of the formula II to nitrogen and an aryl radical and/or promotes the conversion to the compound I' in another way. Especially suitable is the combination of these two measures with one another and with the performance of step (i) Employing Ultrasound.

Diazonium salts of the formula (II) are common knowledge and can be prepared by common processes, as described, for example, in Organikum, Wiley VCH, 22nd edition. For instance, they are obtainable by diazotizing the corresponding aniline derivative, for example by reacting such an aniline derivative with nitrite in the presence of an acid, for instance semiconcentrated sulfuric acid. Both appropriate aniline derivatives for preparing compounds (II) and aniline derivatives of the formula (III) are known or can be prepared by known processes, for example by hydrogenating or homogeneously reducing correspondingly substituted nitrobenzenes in the presence of a suitable catalyst (for instance with Sn(II) chloride/HCl; cf. Houben Weyl, "Methoden d. org. Chemie" [Methods of Organic Chemistry], 11/1, 422). The preparation of azobenzenes and the substitution of suitable benzenes with ammonia are also common methods. Diazonium salts in which the counterions are selected from the anions of aromatic dicarboximides or disulfonimides can be prepared analogously to M. Barbero et al., Synthesis 1998, 1171-1175.

The reaction in step (i) affords a product of the formula I'

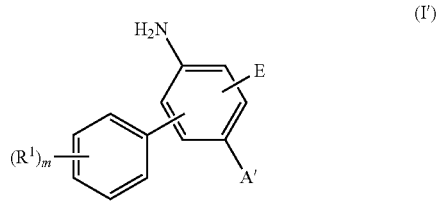

(I')

or in the embodiment A-1.1 (at least predominantly) a product of the formula XI

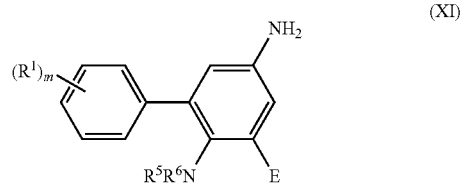

(XI)

in which $R^1$, A', E, $R^5$, $R^6$ and m are each as defined above. It will be appreciated that $R^1$ and m are each as defined in the diazonium salt (II) used and E and A', and $R^5$ and $R^6$ are each as defined in the aniline (III) or (III') used (except that, in the 2nd variant of embodiment A-1 and in embodiment A-1.1, the A' group is converted to an amino group $NH_2$).

Compound (I') is identical to compound (I) with the sole exception that A' in compounds (I') is not H. Therefore, in step (i), compounds (I) in which A is different than H are obtained compounds ($\hat{=}$compounds (I')). When the intention is to prepare compounds (I) in which A is H, another reaction according to step (ii) has to be effected after step (i). In step (ii) any reaction known to those skilled in the art which is suitable for converting an A' group on a phenyl ring to a hydrogen atom can be used. Accordingly, the preparation of compounds (I) in which A is H proceeds from suitable compounds (I') in which A' is a radical which can be converted to hydrogen.

For this purpose, preference is given to using, in step (ii), a compound (I') in which A' is halogen, especially bromine.

When the substituent A' is halogen, especially bromine, it can be exchanged for a hydrogen atom by means of reductive dehalogenation, for example by means of triphenyltin hydride (J. Org. Chem. 1963, 28, 2332), lithium aluminum hydride (J. Chem. Res. 1990, 190) or catalytic hydrogenation.

The isomer separation in steps (i-a) and (i-b-1) in embodiments A-1 and A-1.1 respectively of the process according to the invention can be effected by means of customary separating processes, for example by means of extractive or chromatographic processes, such as column chromatography, HPLC and the like.

The removal of the amino group in step (i-b2) from the aminobiphenyl obtained in step (i) or (i-b1) is effected preferably by diazotization of the amino group ($NH_2$ group) and subsequent reductive removal of the nitrogen.

The diazotization is effected by standard processes, for example by reacting the compound (I') or (I'B) or (XI) with nitrite, e.g. sodium nitrite, in the presence of an acid, for instance semiconcentrated hydrochloric acid, semiconcentrated hydrobromic acid or semiconcentrated sulfuric acid. The reduction (Meerwein reduction) is generally effected in situ. A prerequisite is the selection of the correct solvent. Suitable solvents are especially cyclic ethers, such as tetrahydrofuran and dioxane, and dimethyl-formamide. Processes for diazotization and reduction of the diazonium salts are described, for example, in Organikum, 22nd edition, Wiley-VCH, and in the literature cited therein.

The removal of the $R^6$ radical, which is of course a protecting group, and if required also of the $R^5$ radical (in the case that $R^5$ and $R^6$ together form a protecting group), is effected in step (i-b3) generally under conditions as are customary for the removal of amine protecting groups. The conditions most favorable for the removal of the particular protecting group $R^6$ and optionally $R^5$ are sufficiently well known to the person skilled in the art. For instance, Boc (tert-butoxycarbonyl) can generally be removed most easily with hydrochloric acid or hydrogen chloride in ethereal or alcoholic solution, whereas the hydrolysis can also be effected in basic aqueous solution for acetyl, dimethylformamidino and the imines.

The reaction mixtures obtained in steps (i) and (ii), (i-a) or (i.b3) are worked up and the compound of the formula (I') or (I) or (X) is isolated in a customary manner, for example by an extractive workup, by removing the solvent, for example under reduced pressure, or by a combination of these measures. Further purification can be effected, for example, by crystallization, distillation or by chromatography.

Excess or unconverted reactants (these are in particular the aniline compound (III) or (III')) which is of course preferably used in excess in relation to the diazonium salt (II)) are preferably isolated in the course of workup and reused in step (i).

In a preferred embodiment of the invention, the reaction mixture from step (i) and/or (ii) and/or (i-a) and/or (i-b3), for workup, is extracted more than once with a suitable, essentially water-immiscible organic solvent, and the combined organic phases are concentrated. Examples of suitable, essentially water-immiscible organic solvents are listed above. The product thus isolated can subsequently be retained for uses or sent directly to a use, for example used in a further reaction step, or be purified further beforehand.

Especially when the reaction or the protecting group removal in step (i-b3) has proceeded in acidic solution, preference is given to at least partly neutralizing the reaction mixture before the extraction with an organic solvent, which is generally done by adding a base. Suitable bases are, for example, inorganic bases such as alkali metal hydroxides, e.g. lithium, sodium or potassium hydroxide, alkaline earth metal hydroxides, e.g. magnesium or calcium hydroxide, or alkali metal and alkaline earth metal oxides, e.g. sodium, magnesium or calcium oxide; organic bases such as alkoxides, e.g. sodium methoxide, sodium ethoxide, potassium tert-butoxide and the like; and amines such as diethylamine, triethylamine or ethyldiisopropylamine. Preference is given to the inorganic bases mentioned, which are preferably used as an aqueous solution, and especially to the alkali metal hydroxides mentioned, such as lithium, sodium or potassium hydroxide, preferably in the form of the aqueous solution thereof.

It is also preferable to add a reducing agent, for example an aqueous sodium sulfite solution, to the reaction mixture at this stage.

The invention further provides a process for preparing compounds of the formula (IV)

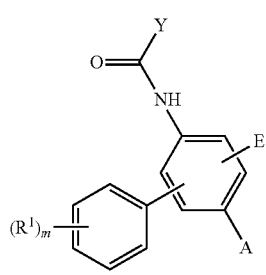

(IV)

in which $R^1$, m, E and A are each as defined above, and

Y is aryl or 5- or 6-membered hetaryl having 1, 2, 3 or 4 heteroatoms which are selected from N, O and S as ring members, where aryl and hetaryl optionally bear 1, 2, 3 or 4 substituents which are selected from halogen, $C_1$-$C_4$-alkyl, $C_1$-$C_4$-haloalkyl, $C_1$-$C_4$-alkoxy and $C_1$-$C_4$-haloalkoxy, comprising the following steps:

(i) reacting a diazonium salt of the general formula (II) with an aniline derivative of the general formula (III),

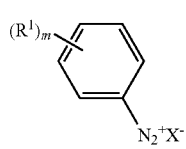

(II)

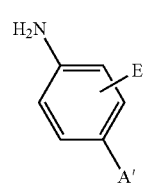

(III)

in which $X^-$, m, $R^1$, E and A' are each as defined above under reaction conditions which can bring about decomposition of the diazonium salt of the formula II to nitrogen and an aryl radical to obtain an aminobiphenyl of the formula (I'),

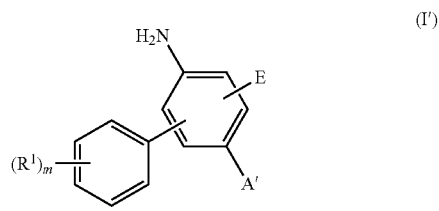

(I')

in which $R^1$, m, E and A' are each as defined above, and (ii) optionally converting the aminobiphenyl of the formula (I') obtained in step (i) to an aminobiphenyl of the formula (I) in which A is hydrogen.

This process is referred to below as process B.

With regard to suitable and preferred compounds (I), (I'), (II) and (III) and to the performance of steps (i) and (ii), reference is made completely to the statements made for process A.

A preferred embodiment of process B (embodiment B-1) relates to processes for preparing compounds of the formula (IVA)

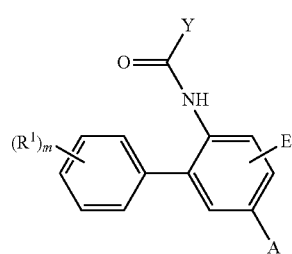

(IVA)

in which $R^1$, m, Y, A and E are each as defined above, comprising the following steps:

(i) reacting a diazonium salt of the formula (II) with an aniline derivative of the formula (III)

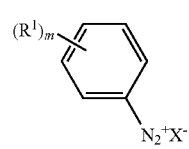

(II)

-continued

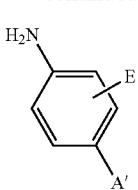
(III)

in which
A' is as defined for A, with the proviso that A' is not hydrogen;
X⁻ is a monovalent anion or the portion of a polyvalent anion equivalent to a monovalent anion, and
m, E and $R^1$ are each as defined above,
under reaction conditions which can bring about decomposition of the diazonium salt of the formula II to nitrogen and an aryl radical
to obtain an aminobiphenyl of the formula (I'),

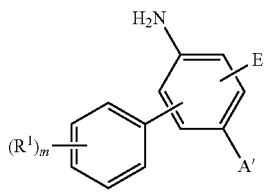
(I')

(i-a) if required, removing isomer I'B from isomer I'A

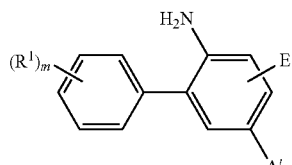
(I'A)

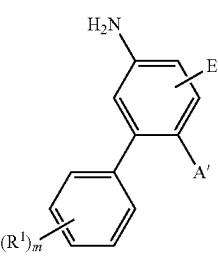
(I'B)

and
(ii) optionally converting the aminobiphenyl of the formula (I'A) obtained in step (i) or (i-a) to an aminobiphenyl of the formula (IA) in which A is hydrogen; or
(i-b1) in the case that A' is $NR^5R^6$ in which
$R^5$ is H; and
$R^6$ is a protecting group and is preferably $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocarbonyl, di-($C_1$-$C_4$-alkyl)-aminocarbonyl, $C_1$-$C_4$-alkylsulfonyl or $C_1$-$C_4$-haloalkylsulfonyl; or
$R^5$ and $R^6$ together form a protecting group and preferably together form a $=CR^{12}$—$NR^{13}R^{14}$ group or, together with the nitrogen atom to which they are bonded, a $C_1$-$C_4$-alkylimino group or an aryl-$C_1$-$C_4$-alkylimino group:
if required, removing isomer I'A from isomer I'B;
(i-b2) removing the amino group of the aminobiphenyl (I'B) obtained in step (i) or (i-b1) to obtain a biphenyl of the formula (XII)

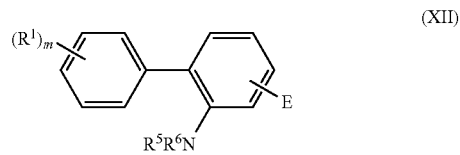
(XII)

and
(i-b3) removing the $R^6$ radical and if required $R^5$ radical to obtain a compound (IA) in which A is H.

With regard to suitable and preferred compounds (I), (I'), (II) and (III) and the performance of steps (i), (ii), (i-a), (i-b1), (i-b2) and (i-b3), reference is made completely to the statements made for process A-1.

A particularly preferred embodiment (embodiment B-1.1) of the 2nd variant of process B-1 relates to a process for preparing N-acyl-2-aminobiphenyls of the general formula (XIII)

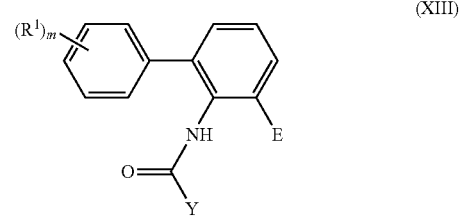
(XIII)

in which
$R^1$, E and m are each as defined above; and
Y is aryl or 5- or 6-membered hetaryl having 1, 2, 3 or 4 heteroatoms selected from N, O and S as ring members, where aryl and hetaryl optionally bear 1, 2, 3, or 4 substituents which are selected from halogen, $C_1$-$C_4$-alkyl, $C_1$-$C_4$-alkoxy and $C_1$-$C_4$-haloalkoxy,
comprising the following steps:
(i) reacting a diazonium salt of the general formula (II) with an aniline derivative of the general formula (III'),

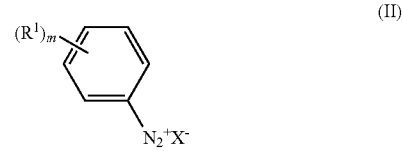
(II)

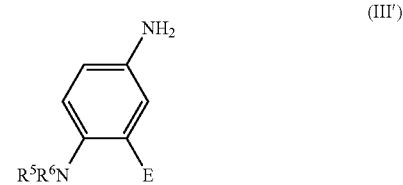
(III')

in which $X^-$, $R^1$, E and m are each as defined in claim 1 and $R^5$ and $R^6$ are each as defined in embodiment A-1.1,
under reaction conditions which can bring about decomposition of the diazonium salt of the formula (II) to nitrogen and an aryl radical,
to obtain an aminobiphenyl of the formula (XI) as defined above;

(i-b2) removing the amino group of the aminobiphenyl obtained in step (i) to obtain a biphenyl of the formula (XII) as defined above; and (i-b3) removing the $R^6$ and if required $R^5$ radical to obtain the compound (X) as defined above.

With regard to suitable and preferred compounds (XIII), (II) and (III') and to the performance of steps (i), (i-b1), (i-b2) and (i-b3), reference is made completely to the statements made for process A-1.1.

The compound I' or I or XI is converted to the compound IV' or IV or XIII by customary prior art processes for amide formation.

Thus, process B, in a preferred embodiment, also comprises the following steps:

(iii) N-acylating the compound of the formula (I') or (I) or (X) obtained in step (i) or step (ii) or step (i-a) or step (i-b3) by reacting with a compound of the general formula (V),

in which Y is as defined above; and W is a leaving group, to obtain a compound of the formula (IV) or of the formula (IV') or (XIII),

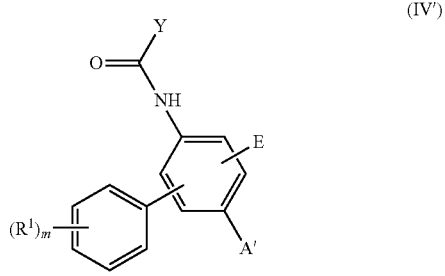

in which $R^1$, m, E and A' are each as defined above, and (iv) optionally converting the compound of the formula (IV') obtained in step (iii) to a compound of the formula (IV) in which A is hydrogen.

The definitions specified as preferred above for $R^1$, m, E, A and A' are also preferred for the compounds of the formulae (IV) and (IV') or (XIII).

Here too, it is the case that the compounds (I) and (I') are identical, with the sole exception that A' in compounds (I'), in contrast to A in compounds (I) is not hydrogen. It is likewise the case that the compounds (IV) and (IV') are identical, with the sole exception that A' in compounds (IV), in contrast to A in compounds (IV), is not hydrogen (except that, in the 2nd variant of embodiment B-1 and in embodiment B-1.1, the group A' is converted to an amino group $NH_2$).

In the compounds of the formulae (V), (IV), (IV') and (XIII), Y is preferably 5- or 6-membered hetaryl having 1, 2 or 3 nitrogen atoms as ring members, where the hetaryl radical optionally bears 1, 2 or 3 substituents which are preferably selected from halogen, $C_1$-$C_4$-alkyl and $C_1$-$C_4$-haloalkyl. The 5- or 6-membered hetaryl radical Y preferably bears 1 or 2 substituents which are preferably selected from halogen, $C_1$-$C_4$-alkyl and $C_1$-$C_4$-haloalkyl.

The 5- or 6-membered hetaryl radicals with 1, 2 or 3 nitrogen atoms as ring members is, for example, pyrrolyl such as 1-, 2- or 3-pyrrolyl, pyrazolyl such as 1-, 3-, 4- or 5-(1H)-pyrazolyl, imidazolyl such as 1-, 3-, 4- or 5-(1H)-imidazolyl, triazolyl such as 1-, 4- or 5-[1,2,3]-(1H)-triazolyl, 2- or 4-[1,2,3]-(2H)-triazolyl, pyridyl such as 2-, 3- or 4-pyridyl, pyrazinyl such as 2-pyrazinyl, pyrimidinyl such as 2-, 4- or 5-pyrimidinyl, pyridazinyl such as 3- or 4-pyridazinyl, or triazinyl such as 2-[1,3,5]-triazinyl. The 5- or 6-membered hetaryl radical with 1, 2 or 3 nitrogen atoms as ring members is preferably pyrazolyl such as 1-, 3-, 4- or 5-(1H)-pyrazolyl, or pyridyl such as 2-, 3- or 4-pyridyl, and especially pyrazol-4-yl or pyridin-3-yl.

Y is especially 2-chloropyrid-3-yl, 1-methyl-3-(trifluoromethyl)pyrazol-4-yl, 1-methyl-3-(difluoromethyl)pyrazol-4-yl or 1,3-dimethyl-5-fluoropyrazol-4-yl.

For the inventive N-acetylation of an aminobiphenyl of the formula (I) or (X) in step (iii), the reagent of the formula (V) used is generally a carboxylic acid or a derivative of a carboxylic acid capable of amide formation, for instance an acid halide, acid anhydride or ester. Accordingly, the leaving group W is typically hydroxyl, halide, especially chloride or bromide, an —$OR^7$ radical or an —O—CO—$R^8$ radical.

When the compound (V) is used in the form of the carboxylic acid (Y—COOH; W=OH), the reaction in step (iii) can be performed in the presence of a coupling reagent. Suitable coupling reagents (activators) are known to those skilled in the art and are, for example, selected from carbodiimides such as DCC (dicyclohexylcarbodiimide) and DCI (diisopropylcarbodiimide), benzotriazole derivatives such as HBTU ((O-benzo-triazol-1-yl)-N,N',N'-tetramethyluronium hexafluorophosphate) and HCTU (1H-benzo-triazolium 1-[bis(dimethylamino)methylene]-5-chlorotetrafluoroborate), and phosphonium activators such as BOP ((benzotriazol-1-yloxy) tris(dimethylamino)-phosphonium hexafluorophosphate), Py-BOP ((benzotriazol-1-yloxy) tripyrrolidine-phosphonium hexafluorophosphate) and Py-BrOP (bromotripyrrolidinephosphonium hexafluorophosphate). In general, the activator is used in excess. The benzotriazole and phosphonium coupling reagents are generally used in a basic medium.

Suitable derivatives of the carboxylic acid Y—COOH are all derivatives which can react with the aminobiphenyl (I), (I') or (X) to give the amide (IV), (IV') or (XIII), for example esters Y—C(O)—$OR^7$ (W=$OR^7$), acid halides Y—C(O)X in which X is a halogen atom (W=halogen), or acid anhydrides Y—CO—O—OC—$R^8$ (W=—O—CO—$R^8$).

The acid anhydride Y—CO—O—OC—$R^8$ is either a symmetric anhydride Y—CO—O—OC—Y ($R^8$=Y) or an asymmetric anhydride in which —O—OC—$R^8$ is a group which can be displaced easily by the aminobiphenyl (I), (I') or (X) used in the reaction. Suitable acid derivatives with which the carboxylic acid Y—COOH can form suitable mixed anhydrides are, for example, the esters of chloroformic acid, for example isopropyl chloroformate and isobutyl chloroformate, or of chloroacetic acid.

Suitable esters Y—$COOR^7$ derive preferably from $C_1$-$C_4$-alkanols $R^7OH$ in which $R^7$ is $C_1$-$C_4$-alkyl, such as methanol, ethanol, propanol, isopropanol, n-butanol, butan-2-ol, isobutanol and tert-butanol, preference being given to the methyl and ethyl esters ($R^7$=methyl or ethyl). Suitable esters may also derive from $C_2$-$C_6$-polyols such as glycol, glycerol, trimethylolpropane, erythritol, pentaerythritol and sorbitol, preference being given to the glyceryl ester. When polyol esters are used, it is possible to use mixed esters, i.e. esters with different $R^7$ radicals.

Alternatively, the ester Y—COOR$^7$ is a so-called active ester, which is obtained in a formal sense by the reaction of the acid Y—COOH with an active ester-forming alcohol, such as p-nitrophenol, N-hydroxybenzotriazole (HOBt), N-hydroxysuccinimide or OPfp (pentafluorophenol).

Alternatively, the reagent (V) used for the N-acylation may possess another common leaving group W, for example thiophenyl or imidazolyl.

The inventive N-acylations with the above-described reagents of the formula (V) can be carried out analogously to known processes.

Preference is given to using, for the N-acylation of compounds (I) or (I') or (X), carbonyl halides (V), especially those in which the leaving group W is chlorine or bromine, and is more preferably chlorine. To this end, preferably from 0.5 to 4 mol and especially from 1 to 2 mol of the acid chloride are used per 1 mol of the compound (I) or (I') or (X).

Typically, the N-acylation of an aminobiphenyl (I) or (I') or (X) is carried out with an acid chloride (V) in the presence of a base, for instance triethylamine, in which case generally from 0.5 to 10 mol, especially from 1 to 4 mol, of the base per 1 mol of the acid chloride are used.

Frequently, a compound of the formula (IV) or (IV') or (XIII) will be prepared by initially charging the appropriate compound (I) or (I') or (X) together with the base, preferably in a solvent, and adding the acid chloride stepwise, optionally dissolved in a solvent, at a temperature in the range from about −30° C. to 50° C., especially from 0° C. to 25° C. Typically, reaction is then allowed to continue at elevated temperature, for instance in the range from 0° C. to 150° C., especially from 15° C. to 80° C.

However, the acylation can also be carried out in the absence of a base. To this end, the acylation is performed in a biphasic system. In this case, one of the phases is aqueous and the second phase is based on at least one essentially water-immiscible organic solvent. Suitable aqueous solvents and suitable essentially water-immiscible organic solvents are described above and also in WO 03/37868. This reference, in which further suitable reaction conditions for acylation processes in the absence of bases are also described in general terms, is hereby fully incorporated by reference.

When A or A' in compounds (I) or (I') is an amino group, it is necessary for the selective preparation of compounds (IV) or (IV') to protect this amino group before the reaction in step (iii), in order to prevent the acylation from proceeding on the nitrogen atom of this group. Suitable protecting groups and processes for introducing them are known to those skilled in the art. For example, the compound (I) or (I') can be converted by reaction with Boc anhydride to a compound (I) or (I') in which A or A' is NHR$^6$ in which R$^6$ is tert-butoxycarbonyl. The compound (I) or (I') can be converted by reaction with acetyl chloride to a compound (I) or (I') in which A or A' is NHR$^6$ in which R$^6$ is acetyl.

The compound (I) or (I') can be converted by reaction with dimethylformamide in the presence of POCl$_3$ or thionyl chloride to a compound (I) or (I') in which A or A' is N=C—(CH$_3$)$_2$. The compound (I) or (I') can be converted by reaction with allyl chloride to a compound (I) or (I') in which A or A' is N(CH$_2$—CH=CH$_2$)$_2$. The compound (I) or (I') can be converted by reaction with an aliphatic or aromatic aldehyde to a compound (I) or (I') in which A or A' is N=C—R in which R is $C_1$-$C_3$-alkyl or aryl, such as phenyl. The compound (I) or (I') can be converted by reaction with a $C_1$-$C_4$-alkyl- or arylsulfonyl chloride, especially with methylsulfonyl chloride, to a compound (I) or (I') in which A or A' is NHR$^6$ in which R$^6$ is $C_1$-$C_4$-alkylsulfonyl or arylsulfonyl and especially methylsulfonyl. The compound (I) or (I') can be converted by reaction with an alkylating agent, such as dimethyl sulfate, methyl iodide, methyl bromide, trimethyloxonium tetrafluoroborate or triethyloxonium tetrafluoroborate, to a compound (I) or (I') in which A or A' is (NR$^7$R$^9$R$^9$)$^+$V$^-$ in which R$^7$, R$^9$ and R$^9$ are each $C_1$-$C_4$-alkyl, especially methyl or ethyl, and V$^-$ is a halide anion, sulfate or tetrafluoroborate. Since the introduction of the protecting group at the stage of the compound (I) or (I') does not proceed selectively under some circumstances, it is more favorable in these cases to introduce the protecting group actually before step (i) and thus to use a compound (III) in which A' is a protective amino group. The protecting group can then, if desired, on completion of step (iii) or (iv), be eliminated again by means of known processes, for example by hydrolysis or, in the case of allyl protecting groups, by reaction with a base in the presence of palladium and a nucleophile such as malonic acid.

The reaction in step (iii) affords, according to whether step (ii) has been carried out or not, a product of the formula (IV) in which A is hydrogen or has a different definition (=compound (IV')).

It will be appreciated that, in the compounds (IV), (IV') and (XIII), R$^1$ and m are each as defined in the diazonium salt (II) used in step (i), A' is as defined in the aniline (III) used, A is as defined for A' in the aniline (III) used or is, when step (ii) has been carried out, hydrogen, and Y is as defined in the acylating agent (V) used.

When the intention is to prepare compounds (IV) in which A is hydrogen, either step (i) must be followed by a reaction in step (ii) or, alternatively, after step (iii), a reaction in step (iv) must be carried out. Alternatively, the procedure is as per the 2nd variant of embodiment B-1 or as per embodiment B-1.1.

With regard to step (ii), reference is made to the remarks regarding process A.

In step (iv), it is possible, as already stated for step (ii), to use any reaction known to those skilled in the art which is suitable for converting an A' group on a phenyl ring to a hydrogen atom. Accordingly, the preparation of compounds (IV) in which A is H proceeds from suitable compounds (IV') in which A' is a radical which can be converted to hydrogen.

For this purpose, preference is given to using, in step (iv), a compound (IV') in which A' is halogen, especially bromine, or NR$^5$R$^6$, especially NH$_2$ or an amino group provided with a protecting group, such as tert-butoxycarbonylamino (NH-Boc), acetylamino, dimethylformamidino, diallylamino, aryl-$C_1$-$C_4$-alkylimino, e.g. benzylimino, $C_1$-$C_4$-alkylsulfonylamino or arylsulfonylamino, or A' is (NR$^7$R$^8$R$^9$)$^+$V$^-$.

When the substituent A' is halogen, especially bromine, it can be exchanged for a hydrogen atom by means of reductive dehalogenation, for example by means of triphenyltin hydride (J. Org. Chem. 1963, 28, 2332), lithium aluminum hydride (J. Chem. Res. 1990, 190), or catalytic hydrogenation.

An amino group as the substituent A' in a compound (IV') can be removed by diazotization and subsequent reduction, which is preferably carried out in situ. When the substituent A' is a protected amino group, it is possible before the diazotization first to carry out customary deprotecting reactions, for example deprotecting with hydrochloric acid or hydrogen chloride in ethereal or alcoholic solution (for Boc), hydrolysis in neutral, acidic or basic aqueous solution (acetyl, dimethylformamidino, imines) or by reaction with a base in the presence of palladium and a carbon nucleophile such as malonic acid (allyl). In the case of particular amino protecting groups, for example in the case of sulfonamides, the deamination can also be carried out without preceding deprotection, for example by the process of Wang et al., J. Org. Chem. 2001, 8293 (use of chloramine). Trialkylammonium substituents [(NR$^7$R$^8$R$^9$)$^+$V$^-$] can be exchanged for hydrogen analogously to the process of MacMillan et al., J. Am. Chem. Oc. 2002, 7894 under mild reductive conditions (sodium). Owing to the mild deamination conditions in the case of sulfonamides and trialkylammonium substituents, it is even possible, instead of the diazotization and subsequent reduction of the amino substituent A', to convert this substituent to a $C_1$-$C_4$-alkylsulfonamide group or an arylsulfonamide group, for example by reacting with a $C_1$-$C_4$-alkylsulfonyl chloride or an arylsulfonyl chloride, preferably with methylsulfonyl chloride, and then to subject it to the above-described deamination reaction, or to convert the amino group to a trialkylammonium substituent by alkylation, for example with one of the aforementioned alkylating agents, and then to subject it to the above-described reductive deamination reaction.

The reaction mixtures obtained in steps (iii) and (iv) are worked up and the compound of the formula (IV') or (IV) or (XIII) is isolated in a customary manner, for example by an aqueous, extractive workup, by removing the solvent, for example under reduced pressure, or by a combination of these measures. Further purification can be effected, for example, by crystallization, distillation or by chromatography.

Processes A and B according to the invention allow preparation, with a low level of complexity and in good yields and selectivities, of aminobiphenyls, preferably 2-aminobiphenyls (I) or (X) which are suitable starting compounds for preparing the carboxamides (IV) and (IV') or (XIII) derived therefrom.

The compounds (XI) are novel and likewise form part of the subject matter of the present invention. In preferred compounds (XI), m is 1 and R$^1$ is 4-fluoro or 4-chloro. In preferred compounds, additionally, R$^5$ is hydrogen and R$^6$ is acetyl, methoxycarbonyl or ethoxycarbonyl.

Some of the compounds I are novel and likewise form part of the subject matter of the present invention. Specifically, the invention relates to the following compounds of the formula Ia

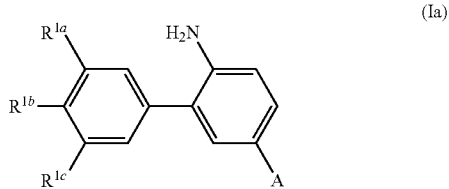

(Ia)

in which:
A is nitro, R$^{1a}$ is H, R$^{1b}$ is Cl and R$^{1c}$ is H;
A is Cl, R$^{1a}$ is H, R$^{1b}$ is Cl and R$^{1c}$ is H;
A is Br, R$^{1a}$ is H, R$^{1b}$ is Cl and R$^{1c}$ is H;
A is NH$_2$, R$^{1a}$ is H, R$^{1b}$ is Cl and R$^{1c}$ is Cl;
A is Br, R$^{1a}$ is H, R$^{1b}$ is Cl and R$^{1c}$ is Cl;
A is NH$_2$, R$^{1a}$ is F, R$^{1b}$ is F and R$^{1c}$ is F;
A is nitro, R$^{1a}$ is F, R$^{1b}$ is F and R$^{1c}$ is F;
A is Cl, R$^{1a}$ is F, R$^{1b}$ is F and R$^{1c}$ is F;
A is Br, R$^{1a}$ is F, R$^{1b}$ is F and R$^{1c}$ is F;
A is F, R$^{1a}$ is F, R$^{1b}$ is F and R$^{1c}$ is F.

EXAMPLES

I. Preparation of the Diazonium Salt

The examples which follow are intended to show by way of example how diazonium salts are prepared. The diazonium salts used in the examples II which follow have been prepared analogously using the correspondingly substituted aniline compounds.

I.1 3,4,5-Trifluorophenyldiazonium tetrafluoroborate

To an ice-cooled solution of 3,4,5-trifluoroaniline (2.00 g; 13.6 mmol) in 50% tetrafluoroboric acid (5.0 ml) was added dropwise, with stirring, a solution of sodium nitrite (1.04 g; 15.1 mmol) in water (1.5 ml). After a further 15 minutes at 0° C., the precipitated solid was filtered off and washed with cold diethyl ether. After drying under reduced pressure, 2.91 g (11.8 mmol; 87% of theory) of the title compound were obtained in the form of a colorless powder.

$^1$H NMR (250 MHz, CD3CN): δ=7.47 (m, 2H)
$^{13}$C NMR (62.9 MHz, CD3CN): δ=120.4 (m, 2CH)

I.2 4-Chlorophenyldiazonium chloride 2.6 g of 98% finely powdered 4-chloroaniline (20.0 mmol) were dissolved in 20 ml of water and 20 ml of 10% hydrochloric acid (the solvent mixture beforehand had been evacuated three times on a rotary evaporator and vented with argon). At 0 to 5° C. under argon, a solution of 1.4 g of sodium nitrite (20.0 mmol) in 10 ml of water (degassed with argon beforehand) was added dropwise to the solution over the course of 10 minutes. The clear diazonium salt solution was stirred at 0° C. for a further 15 minutes and stored under argon.

II. Preparation of Ring-Substituted 2-Aminobiphenyls of the Formula (I)

General Method 40 mmol of an aniline derivative (III) were suspended or dissolved in a mixture of 20 ml of water, 8 ml of 10% by weight aqueous hydrochloric acid and 8 ml of a 1M solution of titanium(III) chloride in 16 ml of 10% by weight aqueous hydrochloric acid (48 mmol of HCl). To this suspension or solution were added, at room temperature, 2 mmol of the tetrafluoroborate salt of a diazonium compound (II) in small portions as a solid over a period of 10 minutes. Once the mixture thus formed had been stirred for a further 15 minutes, a solution of 4.0 g of sodium hydroxide and 4.0 g of sodium sulfite in 40 ml of water was added. The reaction mixture was extracted three times with diethyl ether and the combined organic phases were then washed with saturated sodium chloride solution and dried over sodium sulfate. After the crude product had been concentrated under reduced pressure and purified by column chromatography, the 2-aminobiphenyl was obtained as a light brown oil.

II.1 4'-Fluorobiphenyl-2,5-diamine

Procedure according to the general method.
Yield: 60%
TLC: R$_f$ 0.5 (ethyl acetate)
$^1$H NMR (360 MHz, CDCl$_3$): δ=3.36 (s, 4H), 6.52 (d, J=2.9 Hz, 1H), 6.58 (dd, J=2.9 Hz, J=8.3 Hz, 1H), 6.64 (d, J=8.3 Hz, 1H), 7.11 (dd, J=8.6 Hz, J$_{HF}$=8.6 Hz, 2H), 7.40 (dd, J$_{HF}$=5.4 Hz, J=8.6 Hz, 2H).

$^{13}$C NMR (90.6 MHz, CDCl$_3$): δ=115.5 (d, J$_{CF}$=21.3 Hz, 2×CH), 116.2 (CH), 117.2 (CH), 117.6 (CH), 127.8 (C$_q$), 130.6 (d, J$_{CF}$=7.9 Hz, 2×CH), 135.5 (d, J$_{CF}$=3.4 Hz, C$_q$), 135.7 (C$_q$), 138.5 (C$_q$), 161.9 (d, J$_{CF}$=246.1 Hz, C$_q$).

EI-MS: m/z (%)=203 (14), 202 (100) [M$^+$], 201 (19), 200 (8), 185 (7), 184 (12), 174 (5), 108 (13), 101 (6), 100 (6), 91 (7), 86 (3), 84 (5), 80 (6).

HR-EI-MS: m/z=202.0908, calculated: 202.0906 (C$_{12}$H$_{11}$FN2).

II.2A 4'-Chlorobiphenyl-2,5-diamine

Procedure according to the general method.
Yield: 56%
TLC: R$_f$ 0.5 (ethyl acetate)
$^1$H NMR (500 MHz, CDCl$_3$): δ=3.42 (s, 4H), 6.52 (d, J=2.5 Hz, 1H), 6.60 (dd, J=2.5 Hz, J=8.5 Hz, 1H), 6.64 (d, J=8.5 Hz, 1H), 7.37-7.41 (m, 4H).
$^{13}$C NMR (90.6 MHz, CDCl$_3$): δ=116.2 (CH), 117.1 (CH), 117.2 (CH), 127.2 (C$_q$), 128.5 (2×CH), 130.1 (2×CH), 132.5 (C$_q$), 135.4 (C$_q$), 137.9 (C$_q$), 138.5 (C$_q$).
EI-MS: m/z (%)=220 (34) [$^{37}$Cl-M$^+$], 219 (16), 218 (100) [$^{35}$Cl-M$^+$], 183 (14), 182 (25), 181 (8), 167 (7), 166 (8), 92 (12), 91 (22), 86 (10), 84 (13).
HR-EI-MS: m/z=218.0606, calculated: 218.0611 (C$_{12}$H$_{11}$$^{35}$ClN$_2$).

II.2B 4'-Chlorobiphenyl-2,5-diamine (Batch size with respect to I.2A increased by a factor of 5 with regard to amine (III) used and amount of Ti(III) lowered based on the diazonium salt)

To a solution of 21.6 g (200 mmol) of p-phenylenediamine in 100 ml of water, 55 ml of 10% by weight hydrochloric acid and 25 ml of a 1.1M solution of titanium(III) chloride in 10% by weight of hydrochloric acid were added, at room temperature, 2.24 g (10 mmol) of chlorophenyldiazonium tetrafluoroborate over 15 minutes in small portions. After a further 10 minutes, a solution of 20 g of sodium hydroxide and 20 g of sodium sulfite in 200 ml of water was added dropwise. Extracting the reaction mixture five times with a mixture of 30 ml of diethyl ether and 150 ml of pentane isolated the product. The combined organic phases were subsequently washed with saturated sodium chloride solution and dried over sodium sulfate. After the crude product had been concentrated under reduced pressure, it was purified by column chromatography on silica gel (ethyl acetate).
Yield: 60%

II.2C 4'-Chlorobiphenyl-2,5-diamine

Synthesis of the compound without intermediate isolation of the diazonium salt.

To a solution of finely powdered 4-chloroaniline (2.55 g, 20.0 mmol) in water (20 ml) and 10% hydrochloric acid (20 ml, approx. 3M) (solvent mixture evacuated and vented with argon three times on a rotary evaporator) was added dropwise, at 0° C. under argon, a solution of sodium nitrite (1.38 g, 20.0 mmol) in water (10 ml) (degassed with argon beforehand) over 10 minutes. The clear diazonium salt solution is stirred at 0° C. for a further 15 minutes and kept under argon. For the test which follows, 5 ml of diazonium salt solution are removed (5 ml of salt solution comprise approx. 2 mmol of diazonium salt and 2 mmol of hydrochloric acid).

To a solution of phenylenediamine (4.32 g, 40.0 mmol) in water (25 ml), 10% hydrochloric acid (14 ml) (water-HCl mixture degassed on a rotary evaporator) and titanium(III) chloride (1 ml, approx. 1 mmol) was added dropwise the diazonium salt solution by means of a syringe pump over a period of 6 minutes. After the addition had ended, the mixture was stirred for a further 10 minutes and basified with a solution of sodium sulfite and sodium hydroxide (4 g each in a total of 40 ml of water). After extracting three times with diethyl ether, the combined organic phases are washed with sodium chloride solution and dried over sodium sulfate. After the solvents have been removed, the crude product obtained is an about 1:1 mixture of product and phenylenediamine. The further purification is effected by column chromatography on silica gel (eluent: 100% ethyl acetate).
Yield: 70% (based on 4-chloroaniline)

II.3 2'-Chlorobiphenyl-2,5-diamine

Procedure according to the general method.
Yield: 39%
TLC: R$_f$ 0.5 (ethyl acetate)
$^1$H NMR (360 MHz, CDCl$_3$): δ=3.23 (s, 4H), 6.47 (d, J=2.4 Hz, 1H), 6.62 (dd, J=2.4 Hz, J=8.4 Hz, 1H), 6.66 (d, J=8.4 Hz, 1H), 7.28-7.33 (m, 3H), 7.47-7.50 (m, 1H).
$^{13}$C NMR (90.6 MHz, CDCl$_3$): δ=116.8 (CH), 117.1 (CH), 117.6 (CH), 126.8 (C$_q$), 127.1 (CH), 128.9 (CH), 129.7 (CH), 131.7 (CH), 133.6 (C$_q$), 136.1 (C$_q$), 138.0 (C$_q$), 138.2 (C$_q$).
EI-MS: m/z (%)=220 (34) [$^{37}$Cl-M$^+$], 219 (14), 218 (100) [$^{35}$Cl-M$^+$], 184 (11), 183 (68), 182 (63), 181 (23), 167 (20), 166 (33), 154 (9), 139 (6), 127 (13), 109 (6), 108 (10), 92 (32), 91 (44), 86 (11), 84 (17), 80 (13), 77 (19).
HR-EI-MS: m/z=218.0608, calculated: 262.0611 (C$_{12}$H$_{11}$$^{35}$ClN$_2$).

II.4 2'-Bromobiphenyl-2,5-diamine

Procedure according to the general method.
Yield: 48%
TLC: R$_f$ 0.5 (ethyl acetate)
$^1$H NMR (360 MHz, CDCl$_3$): δ=3.23 (s, 4H), 6.45 (dd, J=0.7 Hz, J=2.4 Hz, 1H), 6.62 (dd, J=2.4 Hz, J=8.4 Hz, 1H), 6.66 (dd, J=0.7 Hz, J=8.4 Hz, 1H), 7.22 (ddd, J=2.0 Hz, J=7.2 Hz, J=8.0 Hz, 1H), 7.30 (dd, J=2.0 Hz, J=8.0 Hz, 1H), 7.37 (ddd, J=1.2 Hz, J=7.2 Hz, J=7.6 Hz, 1H), 7.67 (dd, J=1.2 Hz, J=7.6 Hz, 1H).
$^{13}$C NMR (90.6 MHz, CDCl$_3$): δ=116.8 (CH), 117.1 (CH), 117.4 (CH), 123.9 (C$_q$), 127.7 (CH), 128.6 (C$_q$), 129.1 (CH), 131.6 (CH), 132.9 (CH), 135.9 (C$_q$), 138.2 (C$_q$), 140.1 (C$_q$).
EI-MS: m/z (%)=265 (12), 264 (95) [$^{81}$Br-M$^+$], 263 (16), 262 (100) [$^{79}$Br-M$^+$], 184 (12), 183 (92), 182 (53), 181 (24), 167 (27), 166 (49), 154 (13), 119 (12), 105 (9), 92 (32), 91 (57), 86 (46), 84 (71), 77 (17).
HR-EI-MS: m/z=262.0100, calculated: 262.0106 (C$_{12}$H$_{11}$$^{79}$BrN$_2$).

II.5 4'-Methoxybiphenyl-2,5-diamine

Procedure according to the general method.
Yield: 49%
TLC: R$_f$ 0.4 (ethyl acetate)
$^1$H NMR (360 MHz, CDCl$_3$): δ=3.42 (s, 4H), 3.84 (s, 3H), 6.55-6.59 (m, 2H), 6.64 (d, J=8.1 Hz, 1H), 6.96 (d, J=8.6 Hz, 2H), 7.36 (d, J=8.6 Hz, 2H).
$^{13}$C NMR (90.6 MHz, CDCl$_3$): δ=55.3 (CH$_3$), 114.1 (2×CH), 115.9 (CH), 117.0 (CH), 118.0 (CH), 128.7 (C$_q$), 130.1 (2×CH), 131.8 (C$_q$), 136.0 (C$_q$), 138.2 (C$_q$), 158.7 (C$_q$).
EI-MS: m/z (%)=215 (15), 214 (100) [M$^+$], 199 (21), 182 (4), 171 (4), 170 (4), 169 (4), 154 (6), 148 (5), 133 (6), 123 (7), 119 (17), 109 (10), 108 (23), 107 (10), 105 (14), 91 (15), 85 (11), 80 (8), 71 (16), 70 (13).

HR-EI-MS: m/z=214.1102, calculated: 214.1106 ($C_{13}H_{14}N_2O$).

II.6 4'-Phenoxybiphenyl-2,5-diamine

Procedure according to the general method.
Yield: 15%
TLC: $R_f$ 0.5 (ethyl acetate)
$^1$H NMR (360 MHz, CDCl$_3$): δ=3.45 (s, 4H), 6.58-6.62 (m, 2H), 6.66 (d, J=8.0 Hz, 1H), 7.04-7.09 (m, 4H), 7.13 (tt, J=1.1 Hz, J=7.5 Hz, 1H), 7.37 (dd, J=7.5 Hz, J=8.9 Hz, 2H), 7.40 (d, J=8.8 Hz, 2H).
$^{13}$C NMR (90.6 MHz, CDCl$_3$): δ=116.3 (CH), 117.2 (CH), 118.0 (CH), 118.8 (2×CH), 119.1 (2×CH), 123.4 (CH), 128.4 ($C_q$), 129.8 (2×CH), 130.3 (2×CH), 134.4 ($C_q$), 136.0 ($C_q$), 138.1 ($C_q$), 156.5 ($C_q$), 157.0 ($C_q$).
EI-MS: m/z (%)=277 (23), 276 (100) [M$^+$], 183 (10), 182 (13), 167 (4), 154 (4), 138 (8).
HR-EI-MS: m/z 276.1264, calculated: 276.1263 ($C_{18}H_{16}N_2O$).

II.7 4'-Chloro-5-methoxybiphenyl-2-amine

Procedure according to the general method.
Yield: 15%
TLC: $R_f$ 0.7 (ethyl acetate/dichloromethane (1/20))
$^1$H NMR (360 MHz, CDCl$_3$): δ=3.77 (s, 3H), 3.90 (br s, 2H), 6.70 (d, J=2.7 Hz, 1H), 6.76 (dd, J=0.6 Hz, J=8.6 Hz, 1H), 6.79 (dd, J=2.7 Hz, J=8.6 Hz, 1H), 7.41 (s, 4H).
$^{13}$C NMR: (90.6 MHz, CDCl$_3$): δ=55.8 (CH$_3$), 114.7 (CH), 115.7 (CH), 117.4 (CH), 127.9 ($C_q$), 128.9 (2×CH), 130.4 (2×CH), 133.3 ($C_q$), 136.3 ($C_q$), 137.7 ($C_q$), 153.1 ($C_q$).
EI-MS: m/z (%)=239 (8), 237 (11), 235 (29) [$^{37}$Cl-M$^+$], 234 (14), 233 (93) [$^{35}$Cl-M$^+$], 220 (33), 219 (16), 218 (100), 203 (11), 190 (14), 183 (10), 167 (9), 155 (9), 154 (11), 128 (11), 127 (19), 113 (7), 99 (7), 86 (44), 84 (62).
HR-EI-MS: m/z=233.0601, calculated 233.0608 ($C_{13}H_{12}^{35}ClNO$).

II.8 Methyl 6-amino-4'-chlorobiphenyl-3-carboxylate

Procedure according to the general method.
Yield: 38%
TLC: $R_f$ 0.4 (ethyl acetate/pentane (1/4))
$^1$H NMR (360 MHz, CDCl$_3$): δ=3.86 (s, 3H), 4.20 (br s, 2H), 6.73 (d, J=8.4 Hz, 1H), 7.38 (d, J=8.7 Hz, 2H), 7.44 (d, J=8.4 Hz, 2H), 7.79 (d, J=2.1 Hz, 1H), 7.85 (dd, J=2.1 Hz, J=8.4 Hz, 1H).
$^{13}$C NMR (90.6 MHz, CDCl$_3$): δ=51.7 (CH$_3$), 114.6 (CH), 120.1 ($C_q$), 125.3 ($C_q$), 129.2 (2×CH), 130.4 (2×CH), 130.8 (CH), 132.3 (CH), 133.6 ($C_q$), 136.8 ($C_q$), 147.7 ($C_q$), 167.0 ($C_q$).
EI-MS: m/z (%)=263 (31) [$^{37}$Cl-M$^+$], 262 (18), 261 (98) [$^{35}$Cl-M$^+$], 232 (29), 231 (12), 230 (100), 168 (9), 167 (47), 166 (14), 162 (11), 161 (8), 139 (9), 115 (12), 97 (11), 84 (23).
HR-EI-MS: m/z=261.0559, calculated: 261.0557 ($C_{14}H_{12}^{35}ClNO_2$).

II.9 1-(6-Amino-4'-chlorobiphen-3-yl)ethanone

Procedure according to the general method.
Yield: 35%
TLC: $R_f$ 0.4 (ethyl acetate/pentane (1/4))
$^1$H NMR (360 MHz, CDCl$_3$): δ=2.52 (s, 3H), 4.20 (br s, 2H), 6.74 (d, J=8.4 Hz, 1H), 7.38 (d, J=8.5 Hz, 2H), 7.44 (d, J=8.5 Hz, 2H), 7.73 (d, J=2.2 Hz, 1H), 7.80 (dd, J=2.2 Hz, J=8.4 Hz, 1H).
$^{13}$C NMR (90.6 MHz, CDCl$_3$): δ=26.1 (CH$_3$), 114.5 (CH), 125.1 ($C_q$), 128.1 ($C_q$), 129.3 (2×CH), 130.0 (CH), 130.4 (2×CH), 131.4 (CH), 133.7 ($C_q$), 136.7 ($C_q$), 148.1 ($C_q$), 196.4 ($C_q$).
EI-MS: m/z (%)=245 (17) [$^{37}$Cl-M$^+$], 246 (11), 245 (54) [$^{35}$Cl-M$^+$], 232 (34), 231 (17), 230 (100), 205 (13), 203 (37), 168 (12), 167 (66), 166 (15), 139 (16), 115 (16), 84 (23).
HR-EI-MS: m/z=245.0608, calculated: 245.0608 ($C_{14}H_{12}^{35}ClNO$).

II.10 tert-Butyl (6-amino-4'-chlorobiphen-3-yl)carbamate

To a solution of 0.68 g (3.1 mmol) of 4'-chlorobiphenyl-2,5-diamine in 15 ml of anhydrous dichloromethane was added, under argon at a temperature of 0° C., 0.54 g (2.5 mmol) of di-tert-butyl dicarbonate. The reaction mixture was allowed to warm to room temperature with stirring and was then stirred for a further 12 hours. Subsequently, the solvent was distilled off and the residue was purified by means of column chromatography on silica gel (ethyl acetate/pentane, 1:4→1:1).
Yield: 65%.
TLC: $R_f$ 0.6 (ethyl acetate/pentane (1/2))
$^1$H NMR (250 MHz, CDCl$_3$): δ=1.50 (s, 9H), 3.60 (br s, 2H), 6.32 (s, 1H), 6.70 (d, J=8.3 Hz, 1H), 7.08-7.15 (m, 2H), 7.39 (s, 4H).
$^{13}$C NMR (90.6 MHz, CDCl$_3$): δ=28.4 (3×CH$_3$), 80.1 ($C_q$), 116.4 (CH), 120.5 (br CH), 121.7 (br CH), 126.9 ($C_q$), 128.9 (2×CH), 130.1 ($C_q$), 130.4 (2×CH), 133.2 ($C_q$), 137.4 ($C_q$), 139.0 ($C_q$), (one $C_q$ is absent).

II.11 3',4'-Dichloro-5-fluorobiphenyl-2-amine

Procedure corresponds to the general method, except without addition of sodium sulfite in the workup.
Yield: 32%
TLC: $R_f$ 0.6 (ethyl acetate/pentane (1/4))
$^1$H NMR (250 MHz, CDCl$_3$): δ=3.80 (br s, 2H), 6.72 (dd, $J_{HF}$=4.8 Hz, J=8.8 Hz, 1H), 6.82 (dd, $J_{HF}$=9 Hz, J=3.0 Hz, 1H), 6.90 (ddd, J=3.0 Hz, $J_{HF}$=8.1 Hz, J=8.8 Hz, 1H), 7.30 (dd, J=2.1 Hz, J=8.3 Hz, 1H), 7.52 (d, J=8.3 Hz, 1H), 7.56 (d, J=2.1 Hz, 1H).
$^{13}$C NMR (90.6 MHz, CDCl$_3$): δ=115.8 (d, $J_{CF}$=22.3 Hz, CH), 116.4 (d, $J_{CF}$=22.8 Hz, CH), 117.0 (d, $J_{CF}$=7.8 Hz, CH), 126.1 (d, $J_{CF}$=7.2 Hz, $C_q$), 128.3 (s, CH), 130.9 (s, 2×CH), 131.9 (s, $C_q$), 133.0 (s, $C_q$), 138.4 (d, $J_{CF}$=1.6 Hz, $C_q$), 139.1 (d, $J_{CF}$=2.2 Hz, $C_q$), 156.4 (d, $J_{CF}$=227.6 Hz, $C_q$).
EI-MS: m/z (%)=259 (11) [$^{37}$Cl$_2$-M$^+$], 258 (10), 257 (65) [$^{35}$Cl$^{37}$Cl-M$^+$], 256 (17), 255 (100) [$^{35}$Cl$_2$-M$^+$], 221 (9), 220 (9), 219 (26), 186 (8), 185 (65), 184 (18), 157 (11).

II.12 3',4',5'-Trifluorobiphenyl-2,5-diamine

Procedure corresponding to the general method. In the case of addition of 20 ml of dichloromethane to the reaction mixture, the yield increases to 31%.
Yield: 24% and 31%
TLC: $R_f$ 0.6 (100% ethyl acetate)
$^1$H NMR: (360 MHz, CDCl$_3$): δ=3.35 (br s, 4H), 6.46 (dd, J=0.5 Hz, J=2.4 Hz, 1H), 6.59 (dd, J=2.4 Hz, J=8.3 Hz, 1H), 6.62 (dd, J=0.5 Hz, J=8.3 Hz, 1H), 7.07 (dd, $J_{HF}$=6.6 Hz, $J_{HF}$=8.7 Hz, 2H).
$^{13}$C NMR: (90.6 MHz, CDCl$_3$): δ=113.1 (dd, $J_{CF}$=6.3 Hz, $J_{CF}$=15.2 Hz, 2×CH), 117.0 (CH), 117.1 (CH), 117.6 (CH), 125.6 (m, $C_q$), 135.4 ($C_q$), 135.6 (dt, $J_{CF}$=4.9 Hz, $J_{CF}$=7.9 Hz, $C_q$), 138.7 (td, $J_{CF}$=15.3 Hz, $J_{CF}$=251.4 Hz, $C_q$) 138.8 ($C_q$), 151.1 (ddd, $J_{CF}$=4.3 Hz, $J_{CF}$=9.9 Hz, $J_{CF}$=250.3 Hz, 2×$C_q$).

EI-MS: m/z (%): 239 (14), 238 (100) [M$^+$], 220 (8), 218 (8), 217 (8), 210 (8).

II.13 5,4'-Dichlorobiphenyl-2-amine

Procedure corresponding to the general method.
Yield: yield: 19%
TLC: $R_f$: 0.5 (1:4 ethyl acetate/pentane)
$^1$H NMR: (360 MHz, CDCl$_3$): δ=3.80 (br s, 2H), 6.69 (d, J=8.5 Hz, 1H), 7.07 (d, J=2.5 Hz, 1H), 7.11 (dd, J=2.5 Hz, J=8.5 Hz, 1H), 7.36 (d, J=8.7 Hz, 2H), 7.43 (d, J=8.7 Hz, 2H).
$^{13}$C NMR: (90.6 MHz, CDCl$_3$): δ=116.8 (CH), 123.3 ($C_q$), 127.6 ($C_q$), 128.5 (CH), 129.2 (2×CH), 129.8 (CH), 130.3 (2×CH), 133.7 ($C_q$), 136.7 ($C_q$), 142.0 ($C_q$).
EI-MS: m/z (%)=241 (10) [$^{37}$Cl$_2$-M$^+$], 240 (10), 239 (68) [$^{35}$Cl$^{37}$Cl-M$^+$], 238 (18), 237 [$^{35}$Cl$_2$-M$^+$], 204 (7), 203 (10), 202 (25), 201 (30), 168 (7), 167 (50), 166 (18), 161 (7), 139 (12), 102 (9), 100 (19), 83 (27).
HR-EI-MS: $C_{12}H_9{}^{35}Cl_2N$ calcd.: 237.0112. found.: 237.0107.

II.14 5-Bromo-4'-chlorobiphenyl-2-amine

Gradual addition of 4-chlorophenyldiazonium tetrafluoroborate (0.23 g, 1.0 mmol) to a stirred solution of 4-bromoaniline (0.86 g, 5.0 mmol) in titanium(III) chloride (5 ml, 1M solution in 3M HCl), water (5 ml) and acetonitrile (5 ml). After the addition has ended, the mixture is stirred for a further 10 minutes and basified with 3N sodium hydroxide solution (15 ml). After extraction with diethyl ether and drying of the organic phase over sodium sulfate, the mixture is concentrated under reduced pressure and the crude product is purified by means of column chromatography on silica gel (1:4 ethyl acetate/pentane).
Yield: 18%
TLC: $R_f$: 0.6 (1:4 ethyl acetate/pentane)
$^1$H NMR: (500 MHz, CDCl$_3$): δ=3.71 (br s, 2H), 6.64 (d, J=8.5 Hz, 1H), 7.20 (d, J=2.4 Hz, 1H), 7.24 (dd, J=2.4 Hz, J=8.5 Hz, 1H), 7.36 (d, J=8.6 Hz, 2H), 7.42 (d, J=8.6 Hz, 2H).
$^{13}$C NMR: (90.6 MHz, CDCl$_3$): δ=110.3 ($C_q$), 117.2 (CH), 128.0 ($C_q$), 129.2 (2×CH), 130.3 (2×CH), 131.4 (CH), 132.6 (CH), 133.7 ($C_q$), 136.5 ($C_q$), 142.6 ($C_q$).
EI-MS: m/z(%)=285 (26) [$^{81}$Br$^{37}$Cl-M$^+$], 284 (16), 283 (100), 282 (2), 281 (86) [$^{79}$Br$^{35}$Cl-M$^+$].

II.15 5-Chloro-3',4',5'-trifluorobiphenyl-2-amine

Gradual addition of 3,4,5-trifluorophenyldiazonium tetrafluoroborate (0.25 g, 1.0 mmol) to a stirred solution of 4-chloroaniline (0.86 g, 5.0 mmol) in titanium(III) chloride (5 ml, 1M solution in 3M HCl) and water (5 ml). After the addition has ended, the mixture is stirred for a further 10 minutes and basified with 3N sodium hydroxide solution (15 ml). After extraction with diethyl ether and drying of the organic phase over sodium sulfate, the mixture is concentrated under reduced pressure and the crude product is purified by means of column chromatography on the silica gel (1:4 ethyl acetate/pentane).
Yield: 17%
TLC: $R_f$: 0.7 (1:4 ethyl acetate/pentane)
$^1$H NMR: (360 MHz, CDCl$_3$): δ=3.73 (br s, 2H), 6.69 (d, J=8.5 Hz, 1H), 7.04 (d, J=2.5 Hz, 1H), 7.08 (dd, J=6.5 Hz, J=8.4 Hz, 2H), 7.12 (dd, J=2.5 Hz, J=8.5 Hz, 1H).
$^{13}$C NMR: (90.6 MHz, CDCl$_3$): δ=113.2 (dd, J=6.1 Hz, J=15.2 Hz, 2×CH), 117.1 (CH), 123.4 ($C_q$), 125.5 (m, $C_q$), 129.2 (CH), 129.6 (CH), 134.2 (dt, J=5.0 Hz, J=7.9 Hz, $C_q$), 139.2 (td, J=15.3 Hz, J=251.2 Hz, $C_q$), 141.9 ($C_q$), 151.4 (ddd, J=4.3 Hz, J=10.1 Hz, 251.3 Hz, 2×$C_q$).
EI-MS: m/z(%)=259 (32) [$^{37}$Cl-M$^+$], 258 (15), 257 (100) [$^{35}$Cl-M$^+$].

II.16 3',4'-Dichlorobiphenyl-2,5-diamine

Gradual addition of 3,4-dichlorophenyldiazonium tetrafluoroborate (0.26 g, 1.0 mmol) to a stirred solution of 1,4-phenylenediamine (0.54 g, 5.0 mmol) in titanium(III) chloride (2 ml, 1M solution in 3M HCl) and water (8 ml). After the addition has ended, the mixture is stirred for a further 10 minutes and basified with 3N sodium hydroxide solution (10 ml) and sodium sulfite. After extraction with diethyl ether and drying of the organic phase over sodium sulfate, the mixture is concentrated under reduced pressure and the crude product is purified by means of column chromatography on silica gel (100% ethyl acetate).
Yield: 46%
TLC: $R_f$: 0.6 (100% ethyl acetate)
$^1$H NMR: (360 MHz, CDCl$_3$): δ=3.33 (br s, 4H), 6.49 (d, J=2.3 Hz, 1H), 6.59 (dd, J=2.3 Hz, J=8.4 Hz, 1H), 6.63 (d, J=8.4 Hz, 1H), 7.29 (dd, J=1.9 Hz, J=8.3 Hz, 1H), 7.48 (d, J=8.3 Hz, 1H), 7.56 (d, J=1.9 Hz, 1H).
$^{13}$C NMR: (90.6 MHz, CDCl$_3$): δ=116.9 (CH), 117.3 (CH), 117.5 (CH), 126.3 ($C_q$), 128.4 (CH), 130.6 (CH), 130.9 (CH), 131.1 ($C_q$), 132.7 ($C_q$), 135.6 ($C_q$), 138.8 ($C_q$), 139.7 ($C_q$).
EI-MS: m/z(%)=256 (11), 255 (10), 254 (65), 253 (19), 252 (100).

II.17 4'-Trifluoromethylbiphenyl-2,5-diamine

Yield: 21%
TLC: $R_f$: 0.5 (100% ethyl acetate)
$^1$H NMR: (360 MHz, CDCl$_3$): δ=3.41 (br s, 4H), 6.55 (d, J=2.5 Hz, 1H), 7.63 (dd, J=2.5 Hz, J=8.3 Hz, 1H), 6.68 (d, J=8.3 Hz, 1H), 7.59 (d, J=8.0 Hz, 2H), 7.71 (d, J=8.0 Hz, 2H).
$^{13}$C NMR: (90.6 MHz, CDCl$_3$): δ=116.8 (CH), 117.4 (CH), 117.5 (CH), 124.1 (q, J=271.7 Hz, $C_q$), 125.5 (q, J=3.8 Hz, 2×CH), 127.3 ($C_q$), 129.1 (q, J=32.4 Hz, $C_q$), 129.3 (2×CH), 135.6 ($C_q$), 138.7 ($C_q$), 143.4 (q, J=1.4 Hz, $C_q$).
EI-MS: m/z(%)=253 (16), 252 (100) [M$^+$], 251 (12), 231 (8), 182 (9), 126 (5), 116 (5), 91 (7).
HR-EI-MS: $C_{13}H_{11}F_3N_2$ calcd.: 252.0874. found.: 252.0864.

Biaryl coupling according to embodiment A-1.1

II.18 N-(5-Amino-4'-chlorobiphenyl-2-yl)acetamide 15.3 g of 98% N-(4-aminophenyl)acetamide (100 mmol) were initially charged in 60 ml of water and 36.5 ml of 10% hydrochloric acid (the solvent mixture beforehand had been three times evacuated on a rotary evaporator and vented with argon), and heated to 50° C. At this temperature, 20 mmol of an aryldiazonium chloride solution prepared as described in 1.2 were added dropwise under argon over a period of 75 minutes. During the addition, evolution of nitrogen set in. The mixture was stirred at 50-55° C. for another 2 h. After cooling to 25° C., the mixture was extracted once at autogenous pH (approx. 0.4) with 50 ml of ether. Subsequently, sodium hydroxide solution was used to adjust the pH to 5.5 and the mixture was extracted 4× with 50 ml of ether. The ether extracts obtained at pH 5.5 were combined, washed twice with 50 ml of water and dried over magnesium sulfate. After concentration on a rotary evaporator under reduced pressure, 1.2 g of a dark-colored residue remained, which, according to GC, comprised 52 area % of N-(5-amino-4'-chlorobiphenyl-2-yl)acetamide and 9.7 area % of N-(6-amino-4'-chlorobiphenyl-3-yl)acetamide.

The molar masses of the isomers [$^{35}$Cl-M$^+$=260] were confirmed by means of GC-MS. The assignment of the N-(5-amino-4'-chlorobiphenyl-2-yl)acetamide structure as the main product was made by means of $^1$H NMR in CDCl$_3$. The following signals were assigned to the main product:

$^1$H NMR (360 MHz, CDCl$_3$): δ=1.99 (s, 3H), 6.54 (d, $^4$J=2.7 Hz, 1H), 6.67 (dd, $^3$J=8.6 Hz, $^4$J=2.7 Hz, 1H), 7.26 (d, $^3$J=8.5 Hz, 2H), 7.38 (d, $^3$J=8.5 Hz, 2H), 7.66 (d, $^3$J=8.6 Hz, 1H)

II.19 N-(5-Amino-4'-chlorobiphenyl-2-yl)acetamide (with titanium(III) chloride as the reducing agent)

15.3 g of 98% N-(4-aminophenyl)acetamide (100 mmol) were initially charged in 60 ml of water and 36.5 ml of 10% hydrochloric acid (the solvent mixture beforehand had been three times evacuated on a rotary evaporator and vented with argon). Then 10 g of a 15% solution of titanium(III) chloride (10 mmol) in 10% hydrochloric acid were added. Subsequently, at 25° C., 20 mmol of an aryldiazonium chloride solution prepared as described in 1.2 were added dropwise under argon over a period of 70 minutes. During the addition, evolution of nitrogen set in. The mixture was stirred for 12 h. It was extracted once at autogenous pH (approx. 0.7) with 50 ml of ether. Subsequently, sodium hydroxide solution was used to adjust the pH to 5.5 and the mixture was extracted 4× with 50 ml of ether. The ether extracts obtained at pH 5.5 were combined, washed with 50 ml of water and dried over magnesium sulfate. After concentration on a rotary evaporator at standard pressure, 1.2 g of a dark-colored residue remained, which, according to GC, comprised 58.5 area % of N-(5-amino-4'-chlorobiphenyl-2-yl)-acetamide, 7.7 area % of N-(6-amino-4'-chlorobiphenyl-3-yl)acetamide and 20.9% 4-chloroaniline.

III. Preparation of N-acylated 2-aminobiphenyls of the Formula (IV)

III.1 tert-Butyl {4'-chloro-6-[(2-chloropyridine-3-carbonyl)amino]biphen-3-yl}carbamate To a solution of 0.43 g (1.4 mmol) of tert-butyl (6-amino-4'-chlorobiphen-3-yl)carbamate and 0.70 ml (0.51 g, 5.1 mmol) of triethylamine in 15 ml of dichloromethane was added slowly, at a temperature of 0° C., a solution of 0.37 g (2.1 mmol) of 2-chloronicotinyl chloride in 3 ml of dichloromethane (3 ml), and the mixture was stirred at 0° C. for a further 30 minutes. The reaction mixture was then allowed to warm to room temperature while stirring and heated under reflux for 1 hour. The reaction mixture was finally extracted by shaking with water and saturated sodium chloride solution, the organic phase was concentrated under reduced pressure and the residue was purified by means of column chromatography on silica gel (ethyl acetate/pentane, 3:1→1:1, then ethyl acetate).

Yield: 74%.

TLC: R$_f$ 0.5 (ethyl acetate/pentane (1/1))

$^1$H NMR (360 MHz, CDCl$_3$): δ=1.49 (s, 9H), 6.76 (s, 1H), 7.26 (dd, J=2.6 Hz, J=8.8 Hz, 1H), 7.29-7.32 (m, 1H), 7.30 (d, J=8.6 Hz, 2H), 7.38 (d, J=8.6 Hz, 2H), 7.47 (s, 1H), 8.06 (dd, J=1.9 Hz, J=7.7 Hz, 1H), 8.10 (s, 1H), 8.17 (d, J=8.8 Hz, 1H), 8.39 (dd, J=1.9 Hz, J=4.7 Hz, 1H).

$^{13}$C NMR (90.6 MHz, CDCl$_3$): δ=28.3 (3×CH$_3$), 80.7 (C$_q$), 118.6 (CH), 120.1 (CH), 122.8 (CH), 123.4 (CH), 129.1 (2×CH), 129.2 (C$_q$), 130.6 (2×CH), 131.1 (C$_q$), 133.6 (C$_q$), 134.3 (C$_q$), 135.8 (C$_q$), 136.1 (C$_q$), 139.9 (CH), 146.7 (C$_q$), 151.1 (CH), 152.7 (C$_q$), 162.5 (C$_q$).

ESI-MS: m/z=460 [$^{37}$Cl-M$^+$+H], 458 [$^{35}$Cl-M$^+$+H], 404 [$^{37}$Cl-M$^+$-C$_4$H$_7$], 402 [$^{35}$Cl-M$^+$-C$_4$H$_7$].

III.2 2-Chloro-N-(4'-chlorobiphen-2-yl)nicotinamide (boscalid)

0.20 g (0.44 mmol) of tert-butyl {4'-chloro-6-[(2-chloropyridine-3-carbonyl)amino]-biphen-3-yl}carbamate was dissolved in 4 ml of 10% hydrochloric acid, 1 ml of isopropanol and 3 ml of methanol, and stirred at a temperature of 50° C. for 90 minutes. The reaction mixture was then cooled to 0° C. and admixed dropwise with 1 ml of an aqueous solution of 0.079 g (1.1 mmol) of sodium nitrite. The mixture was left to stir at 0° C. for another 30 minutes and then at room temperature for 30 minutes. After adding 20 ml of isopropanol, the reaction mixture was heated to 70° C. for 15 minutes. After concentration under reduced pressure, ethyl acetate was added and the aqueous phase was basified with sodium carbonate. The product was extracted with ethyl acetate (3×) and the combined organic phases were washed with saturated sodium chloride solution and dried over sodium sulfate. Concentration under reduced pressure was followed by purification by means of column chromatography on silica gel (ethyl acetate/pentane, 1:1).

Yield: 82%

TLC: R$_f$ 0.8 (ethyl acetate)

$^1$H NMR (500 MHz, CDCl$_3$): δ=7.25-7.27 (m, 2H), 7.34 (d, J=8.3 Hz, 2H), 7.34-7.37 (m, 1H), 7.41-7.46 (m, 1H), 7.44 (d, J=8.3 Hz, 2H), 8.13-8.15 (m, 1H), 8.15 (dd, J=1.8 Hz, J=7.6 Hz, 1H), 8.42 (d, J=8.2 Hz, 1H), 8.45 (J=1.8 Hz, J=4.7 Hz, 1H).

$^{13}$C NMR (90.6 MHz, CDCl$_3$): δ=122.2 (CH), 122.8 (CH), 125.3 (CH), 128.8 (CH), 129.2 (2×CH), 130.2 (CH), 130.7 (2×CH), 131.0 (C$_q$), 132.3 (C$_q$), 134.2 (C$_q$), 134.3 (C$_q$), 136.2 (C$_q$), 140.0 (CH), 146.6 (C$_q$), 151.2 (CH), 162.5 (C$_q$).

ESI-MS: m/z=345 [$^{37}$Cl-M$^+$+H], 343 [$^{35}$Cl-M$^+$+].

The invention claimed is:

1. A process for preparing aminobiphenyls of the formula (I)

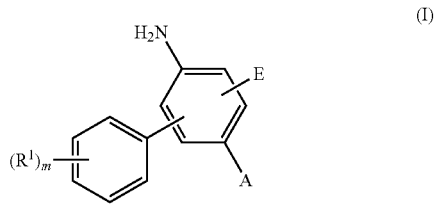

in which m is 0, 1, 2 or 3;

each R$^1$ is independently halogen, C$_1$-C$_4$-alkyl, C$_1$-C$_4$-haloalkyl, C$_1$-C$_4$-hydroxyalkyl, C$_2$-C$_4$-alkenyl, C$_2$-C$_4$-alkynyl, C$_3$-C$_6$-cycloalkyl, C$_1$-C$_4$-alkoxy, C$_1$-C$_4$-haloalkoxy, C$_1$-C$_4$-alkylthio, C$_1$-C$_4$-haloalkylthio, nitro, cyano, SO$_3$R$^3$, SO$_2$R$^3$, SO$_2$NR$^{10}$R$^{11}$, COOR$^2$, COR$^4$, OCOR$^4$, CONR$^{10}$R$^{11}$, NR$^{10}$COR$^4$, NR$^{10}$SO$_2$R$^3$, C$_1$-C$_4$-alkylimino, aryl, aryloxy, arylcarbonyl, aryl-C$_1$-C$_4$-alkyl, arylmethoxycarbonyl, arylalkylimino or 5- or 6-membered hetaryl having 1, 2 or 3 heteroatoms selected from N, O and S, as ring members, where the aryl group and the hetaryl group in the latter radicals optionally bear 1, 2, 3, 4, or 5 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy;

A is hydrogen, $NR^5R^6$, $(NR^7R^8R^9)^+V^-$, halogen, $C_1$-$C_4$-alkyl, $C_1$-$C_4$-haloalkyl, $C_1$-$C_4$-alkylcarbonyl, $C_1$-$C_4$-haloalkylcarbonyl, nitro, $SO_3R^3$, $COOR^2$, $CONR^{10}R^{11}$, $COR^4$ or aryl, where the aryl group optionally bears 1, 2, 3 or 4 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy; and E is hydrogen, halogen, $C_1$-$C_4$-alkyl, $C_1$-$C_4$-haloalkyl, $C_1$-$C_4$-hydroxyalkyl, $C_3$-$C_6$-cycloalkyl, aryl or 5- or 6-membered hetaryl having 1, 2 or 3 heteroatoms selected from N, O and S as ring members, where the aryl and the hetaryl group optionally bear 1, 2, 3, 4 or 5 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy;

in which
each $R^2$ is independently hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from the group consisting of N, O and S as ring members or one cation equivalent;

$R^3$ is hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from the group consisting of N, O and S as ring members;

$R^4$ is hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from the group consisting of N, O and S as ring members;

$R^5$ and $R^6$ are each independently hydrogen, $C_1$-$C_{10}$-alkyl, $C_3$-$C_4$-alkenyl, $C_3$-$C_{10}$-cycloalkyl, $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocabornyl, di-($C_1$-$C_4$-alkyl)aminocarbonyl, $C_1$-$C_4$-alkylsulfonyl, $C_1$-$C_4$-haloalkylsulfonyl, aryl, aryl-$C_1$-$C_4$-alkyl, arylcarbonyl, aryloxycarbonyl or arylmethoxycarbonyl, where the aryl groups of the latter five substituents optionally each bear 1, 2, 3 or 4 substituents which are selected from the group consisting of halogen, nitro, $C_1$-$C_4$-alkyl, $C_1$-$C_4$-haloalkyl, $C_1$-$C_4$-alkoxy and $C_1$-$C_4$-haloalkoxy; or $R^5$ and $R^6$ together form a $=CR^{12}$—$NR^{13}R^{14}$ group or, together with the nitrogen atom to which they are bonded, form a $C_1$-$C_4$-alkylimino group or an aryl-$C_1$-$C_4$-alkylimino group;

$R^7$, $R^8$ and $R^9$ are each independently $C_1$-$C_4$-alkyl;

$R^{10}$ and $R^{11}$ are each independently hydrogen, $C_1$-$C_{10}$-alkyl, $C_1$-$C_{10}$-haloalkyl, $C_1$-$C_{10}$-hydroxyalkyl, $C_2$-$C_4$-alkenyl, $C_2$-$C_4$-alkynyl, $C_3$-$C_{10}$-cycloalkyl, $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylsulfonyl, $C_1$-$C_4$-haloalkylsulfonyl, aryl, aryl-$C_1$-$C_4$-alkyl, arylcarbonyl, aryloxycarbonyl, arylmethoxycarbonyl or 5- or 6-membered hetaryl having 1, 2 or 3 heteroatoms selected from the group consisting of N, O and S ring members, where the aryl and hetaryl groups of the latter 6 substituents optionally each bear 1, 2, 3 or 4 substituents which are selected from the group consisting of halogen, nitro, $C_1$-$C_4$-alkyl, $C_1$-$C_4$-haloalkyl, $C_1$-$C_4$-alkoxy and $C_1$-$C_4$-haloalkoxy;

$R^{12}$, $R^{13}$ and $R^{14}$ are each independently hydrogen, $C_1$-$C_{10}$-alkyl or aryl; and $V^-$ denotes a monovalent anion or the portion of a polyvalent anion equivalent to a monovalent anion;

comprising
(i) reacting a diazonium salt of the formula (II) with an aniline derivative of the formula (III)

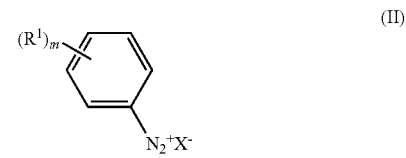

(II)

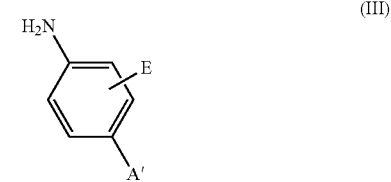

(III)

in which
A' is as defined for A, with the proviso that A' is not hydrogen;
$X^-$ is a monovalent anion or the portion of a polyvalent anion equivalent to a monovalent anion,
under reaction conditions which bring about decomposition of the diazonium salt of the formula II to nitrogen and an aryl radical
to obtain an aminobiphenyl of the formula (I')

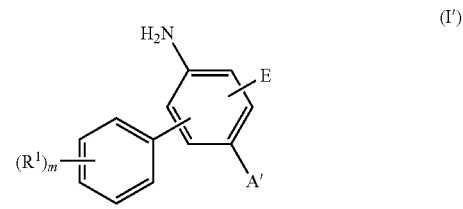

(I')

and
(ii) if desired, converting the aminobiphenyl of the formula (I') obtained in step (i) to an aminobiphenyl of the formula (I) in which A is hydrogen;

where the reaction conditions of step (i) which bring about decomposition of the diazonium salt of the formula II to nitrogen and an aryl radical are selected from the following measures:
performing step (i) in the presence of at least one reducing agent;
performing step (i) while irradiating with electromagnetic radiation in the visible and/or ultraviolet range;
performing step (i) employing ultrasound;
performing step (i) under the conditions of an electrochemical reduction;
performing step (i) in at least one solvent which brings about the free-radical decomposition of the diazonium salt of the formula II to nitrogen and an aryl radical and/or promotes the conversion to the compound I', where the diazonium salt of the formula (II) is used in an amount of 0.001 to 0.9 mol, based in each case on 1 mol of the aniline derivative of the formula (III);

performing step (i) under radiolysis conditions; and performing a combination of at least two of these measures.

2. The process according to claim 1 for preparing 2-aminobiphenyls of the formula (IA),

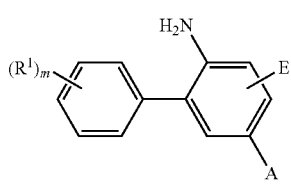

comprising
(i) reacting a diazonium salt of the formula (II) with an aniline derivative of the formula (III)

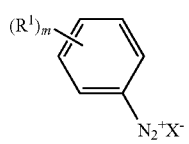

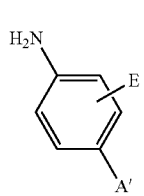

in which
A' is as defined for A, with the proviso that A' is not hydrogen;
$X^-$ is a monovalent anion or the portion of a polyvalent anion equivalent to a monovalent anion,
under reaction conditions which bring about decomposition of the diazonium salt of the formula II to nitrogen and an aryl radical
to obtain an aminobiphenyl of the formula (I'),

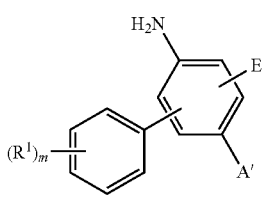

(i-a) if required, removing isomer I'B from isomer I'A

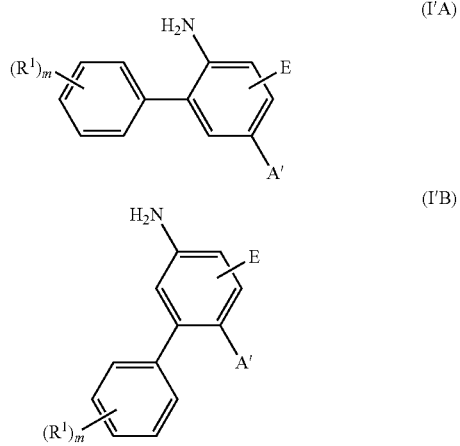

and
(ii) if desired, converting the aminobiphenyl of the formula (I'A) obtained in step (i) or (i-a) to an aminobiphenyl of the formula (IA) in which A is hydrogen; or
(i-b1) in the case that A' is $NR^5R^6$ in which
$R^5$ is H; and
$R^6$ is a protecting group or
$R^5$ and $R^6$ together form a $=CR^{12}$—$NR^{13}R^{14}$ group or, together with the nitrogen atom to which they are bonded, form a $C_1$-$C_4$-alkylimino group or an aryl-$C_1$-$C_4$-alkylimino group;
if required, removing isomer I'A from isomer I'B;
(i-b2) removing the amino group of the aminobiphenyl (I'B) obtained in step (i) or (i-b1) to obtain a biphenyl of the formula (XII)

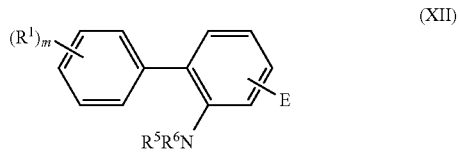

and
(i-b3) removing the $R^6$ and if required $R^5$ radical to obtain a compound (IA) in which A is H;
where the reaction conditions of step (i) which bring about decomposition of the diazonium salt of the formula II to nitrogen and an aryl radical are selected from the group consisting of:
performing step (i) in the presence of at least one reducing agent;
performing step (i) while irradiating with electromagnetic radiation in the visible and/or ultraviolet range;
performing step (i) employing ultrasound;
performing step (i) under the conditions of an electrochemical reduction;
performing step (i) in at least one solvent which brings about the free-radical decomposition of the diazonium salt of the formula II to nitrogen and an aryl radical and/or promotes the conversion to the compound I', where the diazonium salt of the formula (II) is used in an amount of 0.001 to 0.9 mol, based in each case on 1 mol of the aniline derivative of the formula (III);

performing step (i) under radiolysis conditions; and
performing a combination of at least two of these measures.

3. The process according to claim 2 for preparing 2-aminobiphenyls of the general formula (X)

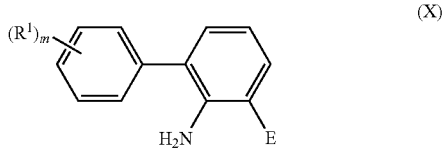

comprising
(i) reacting a diazonium salt of the general formula (II) with an aniline derivative of the general formula (III')

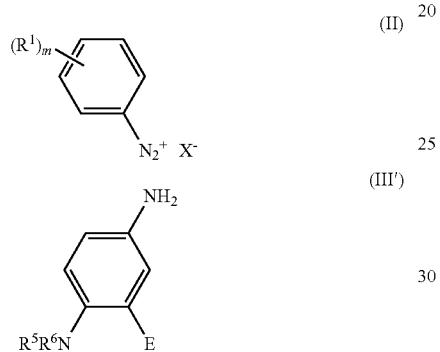

$R^5$ is H; and
$R^6$ is a protecting group; or
$R^5$ and $R^6$ together form a $=CR^{12}-NR^{13}$ group or, together with the nitrogen atom to which they are bonded, form a $C_1$-$C_4$-alkylimino group or an aryl-$C_1$-$C_4$-alkylimino group;
under reaction conditions which can bring about decomposition of the diazonium salt of the formula (II) to nitrogen and an aryl radical
to obtain an aminobiphenyl of the formula (XI)

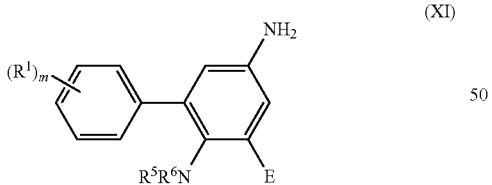

(i-b2) removing the amino group of the aminobiphenyl obtained in step (i) to obtain a biphenyl of the formula (XII)

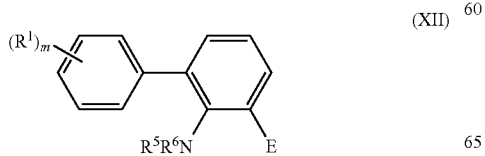

and
(i-b3) removing the $R^6$ and if required $R^5$ radical to obtain the compound (X);
where the reaction conditions of step (i) which bring about decomposition of the diazonium salt of the formula II to nitrogen and an aryl radical are selected from the group consisting of:
performing step (i) in the presence of at least one reducing agent;
performing step (i) while irradiating with electromagnetic radiation in the visible and/or ultraviolet range;
performing step (i) employing ultrasound;
performing of step (i) under the conditions of an electrochemical reduction;
performing step (i) in at least one solvent which brings about the free-radical decomposition of the diazonium salt of the formula II to nitrogen and an aryl radical and/or promotes the conversion to the compound XI, where the diazonium salt of the formula (II) is used in an amount of 0.001 to 0.9 mol, based in each case on 1 mol of the aniline derivative of the formula (III');
performing step (i) under radiolysis conditions; and
performing a combination of at least two of these measures.

4. A process for preparing N-acyl-aminobiphenyls of the general formula (IV)

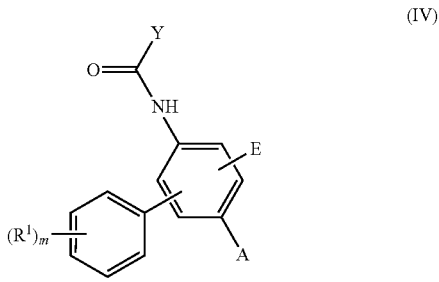

in which
m is 0, 1, 2 or 3;
each $R^1$ is independently halogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, nitro, cyano, $SO_3R^3$, $SO_2R^3$, $COOR^2$, $COR^4$, $OCOR^4$, $CONR^{10}R^{11}$, $NR^{10}COR^4$, $NR^{10}SO_2R^3$, $C_1$-$C_4$-alkylimino, aryl, aryloxy, arylcarbonyl, aryl-$C_1$-$C_4$-alkyl, arylmethoxycarbonyl, arylalkylimino or 5- or 6-membered hetaryl having 1, 2 or 3 heteroatoms selected from N, O and S, as ring members, where the aryl group and the hetaryl group in the latter radicals optionally bear 1, 2, 3, 4, or 5 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy;
A is hydrogen, $NR^5R^6$, $(NR^7R^8R^9)^+V^-$, halogen, $C_1$-$C_4$-alkyl, $C_1$-$C_4$-haloalkyl, $C_1$-$C_4$-alkylcarbonyl, $C_1$-$C_4$-haloalkylcarbonyl, nitro, $SO_3R^3$, $COOR^2$, $CONR^{10}R^{11}$, $COR^4$ or aryl, where the aryl group optionally bears 1, 2, 3 or 4 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy; and
E is hydrogen, halogen, $C_1$-$C_4$-alkyl, $C_1$-$C_4$-haloalkyl, $C_1$-$C_4$-hydroxyalkyl, $C_3$-$C_6$-cycloalkyl, aryl or 5- or 6-membered hetaryl having 1, 2 or 3 heteroatoms selected from N, O and S as ring members, where the aryl and the hetaryl group optionally bear 1, 2, 3, 4 or 5 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy;

in which each $R^2$ is independently hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from the group consisting of N, O and S as ring members or one cation equivalent;

$R^3$ is hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from the group consisting of N, O and S as ring members;

$R^4$ is hydrogen, $C_1$-$C_4$-alkyl, $C_1$-$C_4$-haloalkyl, $C_1$-$C_4$-hydroxyalkyl, $C_2$-$C_4$-alkenyl, $C_2$-$C_4$-alkynyl, $C_3$-$C_6$-cycloalkyl, aryl, 5- or 6-membered hetaryl having 1, 2 or heteroatoms which are selected from the group consisting of N, O and S as ring members;

$R^5$ and $R^6$ are each independently hydrogen, $C_1$-$C_{10}$-alkyl, $C_3$-$C_4$-alkenyl, $C_3$-$C_{10}$-cycloalkyl, $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylaminocabonyl, di-($C_1$-$C_4$-alkyl)aminocarbonyl, $C_1$-$C_4$-alkylsulfonyl, $C_1$-$C_4$-haloalkylsulfonyl, aryl, aryl-$C_1$-$C_4$-alkyl, arylcarbonyl, aryloxycarbonyl or arylmethoxycarbonyl, where the aryl groups of the latter five substituents optionally each bear 1, 2, 3 or 4 substituents which are selected from the group consisting of halogen, nitro, $C_1$-$C_4$-alkyl, $C_1$-$C_4$-haloalkyl, $C_1$-$C_4$-alkoxy and $C_1$-$C_4$-haloalkoxy; or $R^5$ and $R^6$ together form a =$CR^{12}$—$NR^{13}R^{14}$ group or, together with the nitrogen atom to which they are bonded, form a $C_1$-$C_4$-alkylimino group or an aryl-$C_1$-$C_4$-alkylimino group;

$R^7$, $R^8$ and $R^9$ are each independently $C_1$-$C_{10}$-alkyl;

$R^{10}$ and $R^{11}$ are each independently hydrogen, $C_1$-$C_{10}$-alkyl, $C_1$-$C_{10}$-haloalkyl, $C_1$-$C_{10}$-hydroxyalkyl, $C_2$-$C_4$-alkenyl, $C_2$-$C_4$-alkynyl, $C_3$-$C_{10}$-cycloalkyl, $C_1$-$C_4$-alkylcarbonyl, $C_1$-$C_4$-haloalkylcarbonyl, $C_3$-$C_4$-alkenylcarbonyl, $C_1$-$C_4$-alkoxycarbonyl, $C_1$-$C_4$-haloalkoxycarbonyl, $C_3$-$C_4$-alkenyloxycarbonyl, $C_1$-$C_4$-alkylsulfonyl, $C_1$-$C_4$-haloalkylsulfonyl, aryl, aryl-$C_1$-$C_4$-alkyl, arylcarbonyl, aryloxycarbonyl, arylmethoxycarbonyl or 5- or 6-membered hetaryl having 1, 2 or 3 heteroatoms selected from the group consisting of N, O and S ring members, where the aryl and hetaryl groups of the latter 6 substituents optionally each bear 1, 2, 3 or 4 substituents which are selected from the group consisting of halogen, nitro, $C_1$-$C_4$-alkyl, $C_1$-$C_4$-haloalkyl, $C_1$-$C_4$-alkoxy and $C_1$-$C_4$-haloalkoxy;

$R^{12}$, $R^{13}$ and $R^{14}$ are each independently hydrogen, $C_1$-$C_{10}$-alkyl or aryl; and $V^-$ denotes a monovalent anion or the portion of a polyvalent anion equivalent to a monovalent anion;

and

Y is aryl or 5- or 6-membered hetaryl having 1, 2, 3 or 4 heteroatoms which are selected from the group consisting of N, O and S as ring members, where aryl and hetaryl optionally bear 1, 2, 3 or 4 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy, comprising (i) reacting a diazonium salt of the general formula (II) with an aniline derivative of the general formula (III)

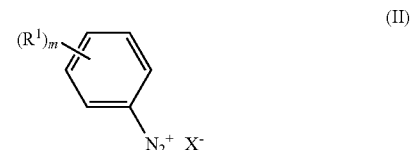

(II)

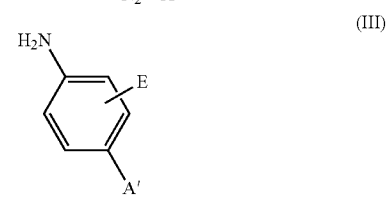

(III)

in which

A' is as defined for A, with the proviso that A' is not hydrogen;

$X^-$ is a monovalent anion or the portion of a polyvalent anion equivalent to a monovalent anion, under reaction conditions which bring about decomposition of the diazonium salt of the formula II to nitrogen and an aryl radical, to obtain a 2-aminobiphenyl of the formula (I')

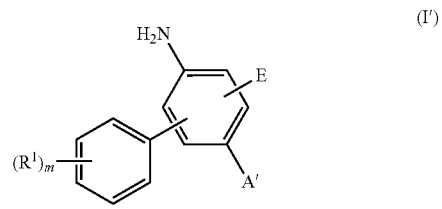

(I')

and (ii) optionally converting the aminobiphenyl of the formula (I') obtained in step (i) to an aminobiphenyl of the formula (I) in which A is hydrogen;

(iii) N-acylating the compound of formula (I') or (I) obtained in step (i) or step (ii) by reacting the compound of formula (I') or (I) with a compound of the general formula (V),

(V)

in which

W is a leaving group, to obtain a compound of the formula (IV) or (IV'),

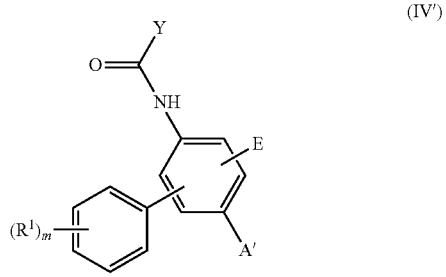

and (iv) if desired converting the compound of the formula (IV') obtained in step (iii) to a compound of the formula (IV) in which A is hydrogen;

where the reaction conditions of step (i) which bring about decomposition of the diazonium salt of the formula II to nitrogen and an aryl radical are selected from the group consisting of:

performing step (i) in the presence of at least one reducing agent;

performing step (i) while irradiating with electromagnetic radiation in the visible and/or ultraviolet range;

performing step (i) employing ultrasound;

performing step (i) under the conditions of an electrochemical reduction;

performing step (i) in at least one solvent which brings about the free-radical decomposition of the diazonium salt of the formula II to nitrogen and an aryl radical and/or promotes the conversion to the compound I', where the diazonium salt of the formula (II) is used in an amount of 0.001 to 0.9 mol, based in each case on 1 mol of the aniline derivative of the formula (III);

performing step (i) under radiolysis conditions; and performing a combination of at least two of these measures.

5. The process according to claim 1, wherein step (i) is performed in at least one solvent which brings about the free-radical decomposition of the diazonium salt of the formula II to nitrogen and an aryl radical and/or promotes conversion to the compound I' or XI,

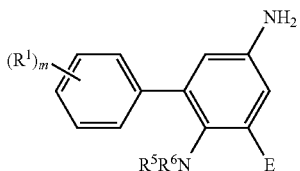

where the diazonium salt of the formula (II) is used in an amount of 0.001 to 0.9 mol based in each case on 1 mol of the aniline derivative of the formula (III).

6. The process according to claim 1, wherein the diazonium salt of the formula (II) is used in an amount of 0.001 to 0.9 mol, based in each case on 1 mol of the aniline derivative of the formula (III).

7. The process according to claim 1, wherein the reaction of the diazonium salt of the formula (II) with the aniline derivative of the formula (III) is effected in a solvent which has been at least partly freed of oxygen.

8. The process according to claim 1, wherein the reaction is effected in an aqueous solvent.

9. The process according to claim 8, wherein the aqueous solvent is water or dilute hydrochloric acid.

10. The process according to claim 1, wherein, in the case that A' is $NR^5R^6$ in which $R^5$ and $R^6$ are each independently hydrogen, $C_1$-$C_4$-alkyl, $C_3$-$C_4$-alkenyl, $C_3$-$C_{10}$-cycloalkyl, aryl or aryl-$C_1$-$C_4$-alkyl, halogen, $C_1$-$C_4$-alkyl, $C_1$-$C_4$-haloalkyl, $C_1$-$C_4$-alkylcarbonyl, $C_1$-$C_4$-haloalkylcarbonyl, nitro, $SO_3R^3$, $COOR^2$, $CONR^{10}R^{11}$, $COR^4$ or aryl optionally substituted, step (i) is performed at a pH of 5 to 9.

11. The process according to claim 1, wherein, in the case that A' is $NR^5R^6$ in which $R^5$ is H and $R^6$ is a protecting group, or $R^5$ and $R^6$ together form a $=CR^{12}$—$NR^{13}R^{14}$ group or, together with the nitrogen atom to which they are bonded, form a $C_1$-$C_4$-alkylimino group or an aryl-$C_1$-$C_4$-alkylimino group, or together with the nitrogen atom to which they are bonded form a $C_1$-$C_4$-alkylimino group or an aryl-$C_1$-$C_4$-alkylimino group, step (i) is performed at a pH of 0 to 7.

12. The process according to claim 1, wherein $X^-$ is selected from the group consisting of $Hal^-$, $BF_4^-$, $PF_6^-$, $SbF_6^-$, $½SO_4^{2-}$, acetate, trifluoroacetate, trichloroacetate, anions of aromatic 1,2-dicarboximides and anions of aromatic 1,2-disulfonimides.

13. The process according to claim 1, wherein, in compound I, $R^1$ is halogen, $C_1$-$C_4$-alkoxy, $C_1$-$C_4$-haloalkoxy or aryloxy, where the aryl group in aryloxy optionally bears 1, 2 or 3 substituents which are selected from the group consisting of halogen, $C_1$-$C_4$-alkyl and $C_1$-$C_4$-alkoxy, and m is 1 or 2.

14. The process according to claim 3, wherein, in compounds X and in the parent compounds III', $R^1$ is halogen, $C_1$-$C_4$-alkyl, $C_1$-$C_4$-haloalkyl, $C_1$-$C_4$-alkoxy, haloalkoxy or aryloxy, where the aryl group in aryloxy optionally bears 1, 2 or 3 substituents which are selected from the group consisting of halogen, $C_1$-$C_4$-alkyl and $C_1$-$C_4$-alkoxy, and m is 1 or 2.

15. The process according to claim 13, wherein $R^1$ is 2-F, 4-F, 2-Cl, 4-Cl, 2-Br, 4-Br, 2-methoxy, 4-methoxy, 2-phenoxy, 4-phenoxy, 3,4-$F_2$ or 3,4-$C_{12}$.

16. The process according to claim 14, wherein $R^1$ is 2-$CH_3$, 3-$CH_3$, 4-$CH_3$, 2-F, 3-F, 4-F, 2-Cl, 3-Cl, 4-Cl, 2-Br, 3-Br, 4-Br, 2-methoxy, 3-methoxy, 4-methoxy, 2-$CF_3$, 3-$CF_3$, 4-$CF_3$, 2-$OCF_3$, 3-$OCF_3$ or 4-$OCF_3$.

17. The process according to claim 16, wherein A is hydrogen, bromine, chlorine, fluorine, $C_1$-$C_4$-alkylcarbonyl, $C_1$-$C_4$-alkoxycarbonyl or $NR^5R^6$, and A' is bromine, chlorine, fluorine, $C_1$-$C_4$-alkylcarbonyl, $C_1$-$C_4$-alkoxycarbonyl or $NR^5R^6$.

18. The process according to claim 17, wherein $R^5$ is hydrogen and $R^6$ is selected from the group consisting of hydrogen, $C_1$-$C_4$-alkylcarbonyl, $C_1$-$C_4$-alkoxycarbonyl, $C_3$-$C_4$-alkenyloxycarbonyl, $C_1$-$C_4$-alkylaminocarbonyl, di-($C_1$-$C_4$-alkyl)aminocarbonyl, benzyl, methylbenzyl, methoxybenzyl, benzyloxycarbonyl and fluorenylmethoxycarbonyl.

19. The process according to claim 18, wherein E is hydrogen.

20. The process according to claim 18, wherein W is halogen.

21. The process according to claim 20, wherein Y is 5- or 6-membered hetaryl having 1, 2 or 3 nitrogen atoms as ring members, where the hetaryl optionally bears 1, 2 or 3 substituents which are selected from the group consisting of halogen, $C_1$-$C_4$-alkyl and $C_1$-$C_4$-haloalkyl.

22. The process according to claim 21, wherein Y is selected from the group consisting of 2-chloropyrid-3-yl, 1-methyl-3-(trifluoromethyl)pyrazol-4-yl, 1-methyl-3-(difluoromethyl)pyrazol-4-yl and 1,3-dimethyl-5-fluoropyrazol-4-yl.

23. The process according to claim 4, wherein, in compounds I and IV, A is selected from the group consisting of hydrogen, bromine and $NR^5R^6$, and, in compounds I' and III, A' is selected from the group consisting of bromine and $NR^5R^6$.

24. The process according to claim 4, wherein, in compounds I and IV, A is hydrogen, $R^1$ is 4-chloro and Y is 2-chloropyrid-3-yl.

25. The process according to claim 4, wherein, in compounds I and IV, A is fluorine, $R^1$ is chlorine, m is 2 and Y is 1-methyl-3-(difluoromethyl)pyrazol-4-yl.

26. The process according to claim 4, wherein, in compounds I and IV, A is hydrogen, $R^1$ is fluorine, m is 3 and Y is 1-methyl-3-(difluoromethyl)pyrazol-4-yl.

* * * * *

UNITED STATES PATENT AND TRADEMARK OFFICE
CERTIFICATE OF CORRECTION

PATENT NO.           : 8,637,707 B2                                    Page 1 of 1
APPLICATION NO.  : 13/001685
DATED                    : January 28, 2014
INVENTOR(S)          : Michael Keil et al.

It is certified that error appears in the above-identified patent and that said Letters Patent is hereby corrected as shown below:

In the Claims

In claim 1,
  col. 47, line 56, delete "$C_1$-$C_4$-alkyl" and insert therefore --$C_1$-$C_{10}$-alkyl--.

In claim 3,
  col. 51, line 37, delete "=$CR^{12}$–$NR^{13}$" and insert therefore --=$CR^{12}$–$NR^{13}R^{14}$--.

In claim 4,
  col. 52, line 48, after "$SO_2R^3$," insert --$SO_2NR^{10}R^{11}$--.

In claim 10,
  col. 56, line 11, delete "$C_1$-$C_4$-alkyl" and insert therefore --$C_1$-$C_{10}$-alkyl--.

In claim 14,
  col. 56, line 36, delete "haloalkoxy" and insert therefore --$C_1$-$C_4$-haloalkoxy--.

In claim 15,
  col. 56, line 42, delete "3,4-$C_{12}$" and insert therefore --3,4,-$Cl_2$--.

Signed and Sealed this
Thirtieth Day of June, 2015

Michelle K. Lee
*Director of the United States Patent and Trademark Office*